US011013694B2

(12) United States Patent
Yan et al.

(10) Patent No.: US 11,013,694 B2
(45) Date of Patent: *May 25, 2021

(54) FORMULATION OF A MICRO DROP PILL AND THE PREPARATION METHOD THEREOF

(71) Applicant: TASLY PHARMACEUTICAL GROUP CO., LTD., Tianjin (CN)

(72) Inventors: Xijun Yan, Tianjin (CN); Naifeng Wu, Tianjin (CN); Kaijing Yan, Tianjin (CN); Xiaobing Sun, Tianjin (CN); Shunnan Zhang, Tianjin (CN); Zhengliang Ye, Tianjin (CN); Hai'ou Dong, Tianjin (CN); Hongbo Zhang, Tianjin (CN); Wensheng Zhang, Tianjin (CN); Lihong Zhou, Tianjin (CN); Chenming Li, Tianjin (CN); Cong Chen, Tianjin (CN); Xiaofeng Liu, Tianjin (CN); Shiqing Wang, Tianjin (CN); Changsheng Rong, Tianjin (CN); Yongfeng Zheng, Tianjin (CN); Lijun Fan, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,857

(22) Filed: May 24, 2019

(65) Prior Publication Data

US 2019/0274962 A1    Sep. 12, 2019

Related U.S. Application Data

(63) Continuation of application No. 14/903,896, filed as application No. PCT/CN2014/082104 on Jul. 11, 2014, now abandoned.

(30) Foreign Application Priority Data

Jul. 11, 2013   (CN) .......................... 201310290966.9
Jul. 11, 2013   (CN) .......................... 201310290967.3
Jul. 11, 2013   (CN) .......................... 201310290968.8
Jul. 11, 2013   (CN) .......................... 201310291465.2

(51) Int. Cl.
*A61K 9/20* (2006.01)
*A61K 36/537* (2006.01)
*A61K 36/258* (2006.01)
*A61K 45/06* (2006.01)
*A61J 3/06* (2006.01)
*A61K 9/50* (2006.01)
*A61K 36/48* (2006.01)
*A61K 36/481* (2006.01)

(52) U.S. Cl.
CPC .............. *A61K 9/2095* (2013.01); *A61J 3/06* (2013.01); *A61K 9/2027* (2013.01); *A61K 9/2054* (2013.01); *A61K 9/2059* (2013.01); *A61K 9/5015* (2013.01); *A61K 9/5026* (2013.01); *A61K 9/5042* (2013.01); *A61K 9/5089* (2013.01); *A61K 36/258* (2013.01); *A61K 36/48* (2013.01); *A61K 36/481* (2013.01); *A61K 36/537* (2013.01); *A61K 45/06* (2013.01)

(58) Field of Classification Search
CPC ...................................................... A61K 9/2895
See application file for complete search history.

(56) References Cited

U.S. PATENT DOCUMENTS

| 3,436,837 | A | 4/1969 | Abelow et al. |
| 5,254,294 | A | 10/1993 | Wunderlich et al. |
| 6,080,429 | A | 6/2000 | Cleland et al. |
| 8,568,628 | B2 | 10/2013 | Norikane et al. |
| 8,945,657 | B2 | 2/2015 | Wang |
| 9,987,320 | B2 | 6/2018 | Yan et al. |
| 9,999,630 | B2 | 6/2018 | Yan et al. |

(Continued)

FOREIGN PATENT DOCUMENTS

| CN | 2508752 Y | 9/2002 |
| CN | 1421241 A | 6/2003 |

(Continued)

OTHER PUBLICATIONS

Sun, X. et al. "Method for preparing dropping pills with cooling air and equipment for using the method", CN 101279220 A, Oct. 8, 2008, English translation.*
Sun, X. et al. "Method for preparing dripping pills with cooling air and equipment fo rusing the method", CN 101279220 A, Oct. 8, 2008, English translation (PTO-138746).*
Wu and Bai "Solid Dispersion Technology," *NEI Mongol Journal of Traditional Chinese Medicine* 3 pages (Jul. 2013)(w/English Abstract).
Allgaier Process Technology, "Fluidised-bed technology for product finishing," 10 pages (Mar. 2009).

(Continued)

*Primary Examiner* — Gina C Justice
(74) *Attorney, Agent, or Firm* — Klarquist Sparkman, LLP

(57) ABSTRACT

The present invention relates to a preparation method for a traditional Chinese medicine drop pill and a traditional Chinese medicine micro drop pill prepared by using the method, and in particular, the present invention relates to a micro drop pill preparation method with high drug-loading capacity, simple preparation process and high production rate and a micro drop pill prepared by using the method. Specially, The drop pill preparation method used comprises the following steps: (1) material melting step: heat melting a medicine and a drop pill matrix to obtain a molten medicine liquid; (2) dropping step: delivering the molten medicine liquid to a dripper, and acquiring medicine drops of the molten medicine liquid by means of vibration dropping; and, (3) condensation step: cooling the medicine drops with a cooling gas to obtain micro drop pills.

15 Claims, No Drawings

(56) References Cited

U.S. PATENT DOCUMENTS

| | | | |
|---|---|---|---|
| 10,111,811 B2 | 10/2018 | Yan et al. | |
| 10,300,030 B2 | 5/2019 | Yan et al. | |
| 10,626,077 B2 | 4/2020 | Zhou et al. | |
| 2005/0037094 A1 | 2/2005 | Yan et al. | |
| 2006/0199010 A1 | 9/2006 | DiCarlo et al. | |
| 2007/0071834 A1 | 3/2007 | Cheng et al. | |
| 2007/0128272 A1 | 6/2007 | Zerbe et al. | |
| 2010/0151036 A1 | 6/2010 | Wu | |
| 2011/0135748 A1 | 6/2011 | Yang et al. | |
| 2014/0065145 A1 | 3/2014 | Debunne | |
| 2016/0143976 A1 | 5/2016 | Yan et al. | |
| 2016/0166472 A1 | 6/2016 | Yan et al. | |
| 2016/0175336 A1 | 6/2016 | Yan et al. | |
| 2016/0184249 A1 | 6/2016 | Yan et al. | |
| 2016/0200661 A1 | 7/2016 | Zhou et al. | |

FOREIGN PATENT DOCUMENTS

| | | | |
|---|---|---|---|
| CN | 1470255 A | | 1/2004 |
| CN | 1714819 A | | 1/2005 |
| CN | 1596920 A | | 3/2005 |
| CN | 1600318 A | | 3/2005 |
| CN | 1600319 A | | 3/2005 |
| CN | 1618445 A | | 5/2005 |
| CN | 1626121 A | | 6/2005 |
| CN | 1633992 | | 7/2005 |
| CN | 1669573 A | | 9/2005 |
| CN | 1745768 A | | 3/2006 |
| CN | 1745769 A | | 3/2006 |
| CN | 1759855 A | | 4/2006 |
| CN | 1772041 A | | 5/2006 |
| CN | 1775204 A | | 5/2006 |
| CN | 2794513 Y | | 7/2006 |
| CN | 1879697 A | | 12/2006 |
| CN | 2865683 Y | | 2/2007 |
| CN | 1927858 A | | 3/2007 |
| CN | 1939406 A | | 4/2007 |
| CN | 101020028 A | | 8/2007 |
| CN | 200948597 Y | | 9/2007 |
| CN | 101085000 A | | 12/2007 |
| CN | 101143152 | | 3/2008 |
| CN | 101229099 A | | 7/2008 |
| CN | 101279220 A | | 10/2008 |
| CN | 101308339 A | | 11/2008 |
| CN | 101354212 A | | 1/2009 |
| CN | 201200979 Y | | 3/2009 |
| CN | 101439076 | | 5/2009 |
| CN | 201253349 Y | | 6/2009 |
| CN | 101518495 A | | 9/2009 |
| CN | 101579449 A | * | 11/2009 |
| CN | 101584743 A | | 11/2009 |
| CN | 101612195 A | | 12/2009 |
| CN | 101711792 A | | 5/2010 |
| CN | 101744722 A | | 6/2010 |
| CN | 101757475 A | | 6/2010 |
| CN | 201589495 U | | 9/2010 |
| CN | 102048707 A | | 5/2011 |
| CN | 102048967 A | | 5/2011 |
| CN | 102078259 A | | 6/2011 |
| CN | 102119963 A | | 7/2011 |
| CN | 102119964 A | | 7/2011 |
| CN | 2448361 Y | | 9/2011 |
| CN | 102178605 A | | 9/2011 |
| CN | 202027925 U | | 11/2011 |
| CN | 102526186 | | 7/2012 |
| CN | 102526446 A | | 7/2012 |
| CN | 102552256 A | | 7/2012 |
| CN | 102908355 A | | 2/2013 |
| CN | 102988476 A | | 3/2013 |
| CN | 204147280 U | | 2/2015 |
| CN | 204170103 U | | 2/2015 |
| EP | 1741439 A1 | | 1/2007 |
| EP | 2415749 A1 | | 2/2012 |
| EP | 3020407 A1 | | 5/2016 |
| EP | 3020408 A1 | | 5/2016 |
| EP | 3040077 A1 | | 7/2016 |
| FR | 2602986 A2 | | 2/1988 |
| JP | 61270202 A | | 11/1986 |
| JP | S63-277616 A | | 11/1988 |
| JP | 2002104958 A | | 4/2002 |
| JP | 2003300870 A | | 10/2003 |
| JP | 2004514736 A | | 5/2004 |
| JP | 2005306778 A | | 11/2005 |
| JP | 2007505936 A | | 3/2007 |
| JP | 2008540419 A | | 11/2008 |
| JP | 2009511549 A | | 3/2009 |
| JP | 2009539819 A | | 11/2009 |
| JP | 2012229173 A | | 11/2012 |
| KR | 10 2005 0026071 | | 3/2005 |
| TW | 201117839 A | | 6/2011 |
| WO | WO 2002058625 A2 | | 8/2002 |
| WO | WO 2005087242 | | 9/2005 |
| WO | WO 2008126720 A1 | | 10/2008 |
| WO | WO 2008132707 A1 | | 11/2008 |
| WO | WO 2010111935 A1 | | 10/2010 |
| WO | WO 2012016549 A1 | | 2/2012 |

OTHER PUBLICATIONS

Briens et al., "Monitoring fluidized bed drying of pharmaceutical granules," *AAPS PharmSciTech* 11(4): 1612-1618 (Dec. 2010).

Extended European Search Report, dated Nov. 11, 2016, from European Patent Application No. 14823013.9, 10 pages.

He et al., CN 101279220, machine translation, 5 pages (Oct. 8, 2008).

Office Action (in Japanese) dated Aug. 18, 2017, by the Japanese Patent Office for corresponding Japanese Patent Application No. 2016-524678, 7 pp.

Office Action (in Chinese), dated Aug. 24, 2017, from Chinese Patent Application No. 201410330969.5, 4 pages.

Office Action (in Chinese), dated Aug. 25, 2017, from Chinese Patent Application No. 201310290967.3, 44 pages.

Office Action(in Chinese), dated May 28, 2018, from Chinese Patent Application No. 201310290966.9, 7 pages.

Office action, with English-language translation, dated Dec. 26, 2017, by the Eurasian Patent Organization (EAPO) for corresponding Eurasian Patent Application No. 201690209 (4 pages).

Qian et al "Preparation of Rabdosia serra Dropping pills" *Shangdong Pharmaceutical Industry* 22(5): 10-11 (2003).

Rena, Halmurat, and Du Nian Sheng, "Research on the water-soluble component of the roots of Salvia deserta Schang." *Journal of Xinjiang Medical University* 3, 2 pages (Sep. 25, 2002) (with English abstract).

Kikuchi, H., "Handbook of Pharmaceutical Machinery and Engineering [Second Edition]," Chijin Shokan, 2010, pp. 216-218, 278-280 (with English translation of a portion).

*Fragrance Journal*, No. 393, vol. 41, No. 3, p. 98 (2013). See: "Product overview", line 2-9, "The characteristics of the device and the prepared particles," line 1 (with English translation).

Jiang, et al. "The pharmacological actions of danshen ThemeD formulas." *In Dan Shen (Salvia miltiorrhiza) in Medicine*, pp. 19-47. Springer Science + Business Media Dordrecht and People's Medical Publishing House, Dordrecht (2015).

Yinggai Chen, "Lesson of severe hypotension caused by intravenous infusion of nitroglycerin," *China Journal of Modern Medicine*, vol. 7, No. 4, 42 (1997) (with English translation).

Mei Liu et al., "Clinical Observation of Tolerance of intravenous infusion of nitroglycerin in elderly patients with CHD," *Nanfang Journal of Nursing*, vol. 3, No. 5, pp. 7-9 (1996) (with English translation).

"Medicines for preventing angina pectoris," *New Pharmaceutics*, Apr. 1998, 14th Edition, p. 264 (with English translation).

Jiping He et al., "5 cases of hypotension caused by nitroglycerin," *Shanxi Medicine Journal*, vol. 25, No. 5, p. 315 (1996) (with English translation).

Lin Yao et al., "Quantitative determination of multi-components in Compound Danshen Dripping Pill by HPLC method," *Shanghai Medical & Pharmaceutical Journal*, vol. 32, No. 8, pp. 413-415 (Aug. 31, 2011). (with English abstract).

(56) References Cited

OTHER PUBLICATIONS

Qiao et al., "Evaluation of the antioxidant potential of Salvia miltiorrhiza ethanol extract in a rat model of ischemia-reperfusion injury," *Molecules* 16, No. 12, pp. 10002-10012 (Dec. 2, 2011).
Wei, et al., "Analysis of chemical and metabolic components in traditional Chinese medicinal combined prescription containing Radix Salvia miltiorrhiza and Radix Panax notoginseng by LC-ESI-MS methods," *Biomedical Chromatography* vol. 21, No. 8, pp. 797-809 (Apr. 12, 2007).
Peng, Y. Q. "Design of automatic control system in new automatic pulse pill dropping machine." *Pharmaceutical Engineering Design* vol. 23, No. 5, pp. 40-43 (2002) (with English translation).
Yang, Ming, "Dropping Pills," Pharmacy of Chinese Materia Medica, Shanghai Scientific & Technical Publishers, p. 227 (Aug. 31, 2008) (with English translation).
"Agricultural Machinery Testing Technology," Beijing Academy of Agricultural Mechanization, China Agricul Ture Press, China, p. 152 (Jun. 30, 1983) (English translation of cited portion).
Hongfa et al., "Metallurgical Engineering Design," Metallurgical Industry Press Co., Ltd, China, p. 350 (Jun. 30, 2006) (with English translation of portion).
"Mechanical Technical Manual," Japan Mechanical Society, Japan, pp. 10-38 (Dec. 31, 1984) (with English translation of portion).
Liu et al., "Principles and Equipment of Chinese Medicine Pharmaceutical Engineering," China Press of Traditional Chinese Medicine Co. Ltd, China, p. 365 (May 31, 2007) (with English translation of portion).

\* cited by examiner

FORMULATION OF A MICRO DROP PILL AND THE PREPARATION METHOD THEREOF

CROSS REFERENCE TO RELATED APPLICATIONS

This is a continuation of U.S. patent application Ser. No. 14/903,896, filed Jan. 8, 2016, which is the National Stage of International Application No. PCT/CN2014/082104, filed Jul. 11, 2014, which claims priority to Chinese Application No. 201310290966.9, filed Jul. 11, 2013, Chinese Application No. 201310290967.3, filed Jul. 11, 2013, Chinese Application No. 201310290968.8, filed Jul. 11, 2013 and Chinese Application No. 201310291465.2, filed Jul. 11, 2013.

FIELD OF THE INVENTION

The present invention relates to a formulation of a micro drop pill and the preparation method thereof, more particularly, the present invention relates to a micro drop pill preparation method with high drug-loading capacity, simple preparation process and high production rate and a formulation of micro drop pill prepared by the method. The method can be used to prepare an uncoated micro drop pill, a coated micro drop pill and a micro drop pill capsule with high drug-loading capacities.

BACKGROUND OF THE INVENTION

Drop pill, as an important traditional Chinese medicine preparation, has been used widely. In practice, it has the following merits: shortened production cycle, dust pollution-free, high bioavailability, rapid onset of effect, prolonged action in topical administration, reduced volatility of drug, increased drug stability and being easily carried and stored.

However, the preparation method of the traditional drop pill is to drop a molten medicine liquid into an immiscible cooling medium (in most cases, a coolant is used as the cooling medium) to give the drop pill. Because the drop pill is formed mainly by factors of freely-falling gravity, surface tension of medicine liquid and internal stress, the unit drug-loading capacity is small (usually, the drug-loading capacity of the active pharmaceutical ingredient (API) is only about 25 wt %) and the amount of matrix used is very large. This cannot meet the requirement of international market that the maximum daily dosage of polyethylene glycols (PEGs) matrix should not exceed 700 mg. Moreover, it is difficult to prepare the traditional drop pill with a diameter of less than 2.5 mm, so the patients have to take a lot of hard-to-swallow pills each time, which will not satisfy fast-paced trend of modern life, and be prone to the problem of inaccurate dosage. Thus, it is generally unacceptable by the international consumers. In addition, there are a number of shortcomings in the preparation of the traditional drop pills, e.g. low dropping frequency, poor roundness, and a large variation in the pill weight and the particle size of the drop pills. Because the coolant has been used for solidifying the drop pills, the necessary step is needed in the subsequent process to remove the coolant, and the irremovable coolant may cause the problem of residual organic solvent. Besides, drying methods for the traditional drop pill have the defects of prolonged time, uneven drying and easily leading to evaporation of volatile oil-containing products and precipitation of borneol of borneol-containing products during drying.

As a result, how to obtain a micro drop pill with high production rate, reduced amount of matrix, increased drug-loading capacity and smaller particle size is an important subject for the development and exploration of the modern preparation process of the drop pill.

SUMMARY OF THE INVENTION

The objective of the present invention is to provide a simple and high-speed preparation method to prepare a micro drop pill with high drug-loading capacity and small amount of matrix. The preparation method for preparing the micro drop pill comprises the following steps:

(1) Material melting step: heat melting a medicine and a drop pill matrix to obtain a molten medicine liquid;

(2) Dropping step: delivering the molten medicine liquid under pressure to a dripper, and acquiring medicine drops of the molten medicine liquid by means of vibration dropping; and, (3) Condensation step: cooling the medicine drops with a cooling gas to obtain micro drop pills.

Another objective of the present invention is to provide a TCM formulation of micro drop pill. In the micro drop pill, the ratio of the medicine to the drop pill matrix is 1:5~5:1 by weight, and the particle size of the micro drop pill is 0.2 mm~4 mm. Moreover, the micro drop pill is prepared according to the preparation method of the micro drop pill of the present invention, and there is no residual coolant.

In the present invention, the micro drop pill means that the micro drop pill has a smaller particle size compared with the traditional drop pill. More specifically, the micro drop pill refers to the one with a particle size of 0.2 mm~4 mm, especially, the one with a particle size of 0.2 mm~2 mm, preferably 1 mm~2 mm.

In the present invention, the coolant of the drop pill means the coolant commonly-used in the preparation of the traditional drop pill, for example, but not limited to, liquid paraffin, methyl silicone oil and plant oil (soybean oil and castor oil etc.).

In the present invention, the medicine includes any one of TCMs or chemicals that is suitable to be prepared into the drop pills. In terms of the TCMs, the extract is preferred to be used, e.g. *Ginkgo biloba* extract, *Bupleurum* extract, *Salvia militiorrhiza* extract and *Andrographis paniculata* extract, as well as the extracts of Qishenyiqi, Huoxiangzhengqi and Compound *Salvia militiorrhiza*. These extracts can either be commercially available, or prepared by the method known in the prior art. In the present invention, the micro drop pill includes, but is not limited to: Compound *Salvia militiorrhiza* micro drop pill (CSMDP), Qishenyiqi micro drop pill (QMDP), *Salvia militiorrhiza* micro drop pill (SMDP), Huoxiangzhengqi micro drop pill (HMDP), *Andrographis paniculata* micro drop pill (AMDP), Compound *Ginkgo biloba* micro drop pill (CGMDP), Guanxindanshen micro drop pill (GMDP) and Xuesaitong micro drop pill (XMDP) etc. Preferably, the medicines in the present invention are the API of Compound *Salvia militiorrhiza* and the API of Qishenyiqi.

Another objective of the present invention is to provide Compound *Salvia militiorrhiza* micro drop pill prepared by the method of the present invention, characterized in that the ratio of the API of Compound *Salvia militiorrhiza* to the drop pill matrix is 1:5~5:1 by weight, and a particle size of the micro drop pill is 0.2 mm~4 mm, preferably 0.2 mm~2 mm, more preferably 1 mm~2 mm. The API of Compound *Salvia militiorrhiza* is prepared with the following crude drugs by weight parts: *Salvia militiorrhiza* 75.0~90.0 parts, *Panax notoginseng* 10.0~25.0 parts and borneol 0.1~4.0 parts, and is prepared by the preparation method for the micro drop pill of the present invention. There is no residual coolant in the micro drop pills.

Another objective of the present invention is to provide QMDP (Qishenyiqi micro drop pill) prepared by the method of the present invention, characterized in that the ratio of the API of Qishenyiqi to the drop pill matrix is 1:5~5:1 by weight, and the particle size 0.2 mm~4 mm, preferably 0.2 mm~2 mm, more preferably 1 mm~2 mm. The API of Qishenyiqi is prepared by the following crude drugs by weight parts: *Astragalus membranaceus* 100~200 parts, *Salvia militiorrhiza* 50~100 parts, *Panax notoginseng* 10~20 parts and volatile oil from *Lignum dalbergiae odoriferae* 0.5~2 parts, and is prepared by the preparation method for the micro drop pill of the present invention. There is no residual coolant in the micro drop pills.

More specifically, as the first aspect of the invention, the present invention is achieved by the following technical solutions:

1. A preparation method for a micro drop pill comprising the following steps:

(1) Material melting step: heat melting a medicine and a drop pill matrix to obtain a molten medicine liquid;

(2) Dropping step: delivering the molten medicine liquid under pressure to a dripper, and acquiring medicine drops of the molten medicine liquid by means of vibration dropping; and, (3) Condensation step: cooling the medicine drops with a cooling gas to obtain micro drop pills.

2. The preparation method according to the $1^{st}$ paragraph, wherein the method comprises the following steps:

(1) Material melting step: heat melting the medicine and the drop pill matrix at 40° C.~120° C., homogenizing for 0.5~4 hours to obtain a homogenized molten medicine liquid, and the ratio of the medicine to the drop pill matrix is 1:5~5:1 by weight;

(2) Dropping step: delivering the molten medicine liquid under pressure to the dripper, and acquiring medicine drops at a vibration frequency for dropping of 20~300 Hz under a dropping pressure of 0.5~4.0 Bar, a temperature of the dripper of 40° C.~200° C. and a viscosity of the molten medicine liquid of 300~1500 cp; and, (3) Condensation step: cooling the medicine drops with a cooling gas for forming by solidifying, obtaining micro drop pills having a particle size of 0.2 mm~4 mm, the temperature of the cooling gas is 0° C. or lower.

3. The preparation method according to the $1^{st}$ or $2^{nd}$ paragraph, wherein in Step (1), the drop pill matrix includes one or more selected from the group consisting of PEGs, sorbitol, xylitol, lactitol, maltose, starch, methylcellulose, sodium carboxymethyl cellulose, hydroxypropyl methylcellulose (HPMC), arabic gum, alginic acid, dextrin, cyclodextrin, agar and lactose; preferably solid PEGs, such as PEG-1000, PEG-2000, PEG-3000, PEG-4000, PEG-5000, PEG-6000, PEG-7000 and PEG-8000; more preferably one or more selected from the group consisting of PEG-1000, PEG-2000, PEG-3000, PEG-4000, PEG-6000 and PEG-8000; most preferably PEG-6000, PEG-4000 or the combination of PEG-4000 and PEG-6000.

4. The preparation method according to any one of the $1^{st}$~$3^{rd}$ paragraphs, wherein in Step (1), the temperature for heat melting is at 60~100° C., more preferably at 65~90° C., further preferably 75~85° C.

5. The preparation method according to any one of the $2^{nd}$~$4^{th}$ paragraphs, wherein in Step (1), the homogenizing time preferably is 1~3 hours, further preferably 2 hours.

6. The preparation method according to any one of the $1^{st}$~$5^{th}$ paragraphs, wherein in Step (1), the ratio of the medicine to the drop pill matrix is 1:3~3:1 by weight, preferably 1:(1~3) by weight.

7. The preparation method according to any one of the $1^{st}$~$6^{th}$ paragraphs, wherein in Step (2), the temperature of the dripper is at 40~120° C., preferably at 40~100° C.; the vibration frequency for dropping is preferably at 20~300 Hz, more preferably 50~300 Hz, more preferably 20~200 Hz, more preferably 20~150 Hz, most preferably 50~150 Hz; the vibration mode includes magnetic/electronic vibration or pneumatic vibration.

8. The preparation method according to any one of the $1^{st}$~$7^{th}$ paragraphs, wherein in Step (3), the temperature of the cooling gas is at 0° C.~−150° C., preferably −10°~−140° C., further preferably −40° C.~−140° C., further preferably −60° C.~−140° C., most preferably −80° C.~−120° C.; and the cooling gas is air, nitrogen or inert gas.

9. The preparation method according to any one of the $1^{st}$~$8^{th}$ paragraphs, wherein in Step (3), the particle size of the micro drop pill is 1.0 mm~2.0 mm, preferably 0.5 mm~2 mm.

10. The preparation method according to the $2^{nd}$ paragraph comprising the following steps:

(1) Material melting step: heat melting the medicine and the drop pill matrix at 60° C.~100° C., homogenizing for 1~3 hours to obtain a homogenized molten medicine liquid, the ratio of the medicine to the drop pill matrix is 1:3~3:1 by weight;

(2) Dropping step: delivering the molten medicine liquid under pressure to a dripper, and acquiring medicine drops at a vibration frequency for dropping of 20~200 Hz under a dropping pressure of 0.5~4.0 Bar, the temperature of the dripper of 60° C.~120° C. and a viscosity of the molten medicine liquid of 700~1000 cp; and, (3) Condensation step: cooling the medicine drops with a cooling gas for forming by solidifying, obtaining the micro drop pills having a particle size of 0.5 mm~2 mm, the temperature of the cooling gas is 0° C.~−150° C.

11. The preparation method according to the $2^{nd}$ paragraph comprising the following steps:

(1) Material melting step: charging the medicine and the drop pill matrix into a homogenizer, mixing homogenously at 1000~5000 rpm for 1~200 min, then melting homogenously at 3000~10000 rpm for 1~100 min; during the melting process, the temperature is kept at 60~100° C. to obtain the molten medicine liquid; the ratio of the medicine to the drop pill matrix is 1:5~5:1 by weight;

(2) Dropping step: delivering the molten medicine liquid under pressure to the dripper, and acquiring medicine drops from the dripper by means of vibration dropping at a vibration frequency of 20~300 Hz under a dropping pressure of 0.5~4.0 Bar and the temperature of the dripper of 40° C.~−200° C., the dropping rate is matched with the melting rate in Step (1); and (3) Condensation step: cooling the medicine drops with a cooling gas rapidly to solidify, and obtaining solid drop pills having a particle size of 0.2 mm~4.0 mm; the temperature of the cooling gas is 0° C.~−150° C.

12. The preparation method according to the $11^{th}$ paragraph, wherein in Step (1), the ratio of the medicine to the drop pill matrix is 1:3~3:1 by weight, mixing homogeneously at 3000~5000 rpm for 10~60 min, then melting homogeneously at 4000~9000 rpm for 5~30 min, during the melting process, the temperature is kept at 70~90° C.

13. The preparation method according to the 11$^{th}$ paragraph, wherein in Step (1), the ratio of the medicine to the drop pill matrix is 1:(1~3) by weight, mixing homogeneously at 3000~4000 rpm for 10~30 min, then melting homogeneously at 4000~6000 rpm for 6~30 min, during the melting process, the temperature is kept at 75~85° C.

14. The preparation method according to the 11$^{th}$ paragraph, wherein in Step (2), the temperature of the dripper is at 70~100° C., the vibration frequency for dropping is at 90~200 Hz, the dropping pressure is at 1.0~3.0 Bar; preferably the vibration frequency is at 137 Hz, an acceleration speed is at 4G, the dropping pressure is at 1.8 Bar and the temperature of the dripper is at 75~85° C.

15. The preparation method according to the 11$^{th}$ paragraph, in Step (2), the dropping rate is 10~40 Kg/h, preferably 12~30 Kg/h, further preferably 15~25 Kg/h.

16. The preparation method according to any one of the 1$^{st}$~15$^{th}$ paragraphs, wherein the method additionally comprises a drying step as Step (4): drying the low-temperature drop pills from Step (3) on a fluidized-bed at 40~150° C., preferably at 40~60° C. for 1~4 hours, preferably 1~3 hours, most preferably 2 hours to obtain uncoated drop pills.

17. The preparation method according to the 16$^{th}$ paragraph, wherein in Step (4), a gradient-rising temperature drying method is used as follows: fluidizing at −20~30° C., drying at 15~35° C. for 10~120 min, drying at 35~55° C. for 10~60 min, drying at 55~100° C. for 0~60 min; preferably, the gradient-rising temperature drying method is performed as follows: fluidizing at 0~20° C., drying at 25° C. for 60 min, drying at 45° C. for 30 min, drying at 55° C. for 0~30 min.

18. The preparation method according to any one of the 1$^{st}$~17$^{th}$ paragraphs, wherein the method additionally comprises a coating step as Step (5): coating the uncoated drop pills obtained from Step (4) in a state of fluidization; the concentration of the coating liquid is at 15~25 wt %, preferably 18~20 wt %; the coating material is selected from shellac, CAP (cellulose acetate phthalate), methyl acrylate, methyl methacrylate or Opadry; the ratio of the coating material to the uncoated drop pill is 1:50~1:25 by weight.

19. The preparation method according to any one of the 1$^{st}$~18$^{th}$ paragraphs, wherein the method additionally comprises a pre-mixing step before Step (1): adding the medicine powder or extract with water, stirring for 10 min or longer at 30~80° C. to obtain a pre-mixed medicine material.

As the second aspect of this invention, the present invention includes the following technical solutions:

20. A TCM formulation of micro drop pill, wherein in the micro drop pill, the ratio of the medicine to the drop pill matrix is 1:5~5:1 by weight, a particle size of the micro drop pill is 0.2 mm~4 mm, the micro drop pill is prepared by any one method of the 1$^{st}$~19$^{th}$ paragraphs, and the micro drop pill has no residual coolant.

21. The TCM formulation of micro drop pill according to the 20$^{th}$ paragraph, characterized in that the particle size is 0.2 mm~2 mm.

22. The TCM formulation of micro drop pill according to the 21$^{st}$ paragraph, characterized in that the particle size is 1 mm~2 mm.

23. A Compound Salvia militiorrhiza micro drop pill (CSMDP), wherein the micro drop pill is prepared by the API of Compound Salvia militiorrhiza and the drop pill matrix in a ratio of 1:5~5:1 by weight, the particle size of the Compound Salvia militiorrhiza micro drop pill is 0.2 mm~4 mm, the API of Compound Salvia militiorrhiza is prepared by the following crude drugs by weight parts: Salvia militiorrhiza 75.0~90.0 parts, Panax notoginseng 10.0~25.0 parts and borneol 0.1~4.0 parts, and the micro drop pill is prepared by any one method of the 1$^{st}$~19$^{th}$ paragraphs, and the micro drop pill has no residual coolant.

24. The CSMDP according to the 23$^{rd}$ paragraph, wherein the micro drop pill is prepared by the API of Compound Salvia militiorrhiza and the drop pill matrix in a ratio of 1:3~3:1 by weight.

25. The CSMDP according to the 24$^{th}$ paragraph, wherein the micro drop pill is prepared by the API of Compound Salvia militiorrhiza and the drop pill matrix in a ratio of 1:(1~3) by weight.

26. The CSMDP according to any one of the 23$^{rd}$~25$^{th}$ paragraphs, characterized in that the particle size of the micro drop pill is 0.2 mm~2 mm.

27. The CSMDP according to the 26$^{th}$ paragraph, characterized in that the particle size of the micro drop pill is 1 mm~2 mm.

28. The CSMDP according to any one of the 23$^{rd}$~27$^{th}$ paragraphs, wherein the API of Compound Salvia militiorrhiza is prepared by the following crude drugs by weight parts: Salvia militiorrhiza 80.0~86.0 parts, Panax notoginseng 15.0~18.0 parts and borneol 0.2~2.0 parts.

29. The CSMDP according to any one of the 23$^{rd}$~28$^{th}$ paragraphs, wherein the API of Compound Salvia militiorrhiza is prepared by the following crude drugs by weight parts: Salvia militiorrhiza 82.0~84.0 parts, Panax notoginseng 16.0~17.0 parts and borneol 0.4~1.2 parts.

30. A Qishenyiqi micro drop pill (QMDP), characterized in that the micro drop pill is prepared by the API of Qishenyiqi and the drop pill matrix in a ratio of 1:5~5:1 by weight, the particle size of the Qishenyiqi micro drop pill is 0.2 mm~4 mm, the API is prepared by the following crude drugs by weight parts: Astragalus membranaceus 100~200 parts, Salvia militiorrhiza 50~100 parts, Panax notoginseng 10~20 parts and volatile oil from Lignum dalbergiae odoriferae 0.5~2 parts, the micro drop pill is prepared by any one method of the 1$^{st}$~19$^{th}$ paragraphs, and the micro drop pill has no residual coolant.

31. The QMDP according to the 30$^{th}$ paragraph, wherein the QMDP is prepared by the API of Qishenyiqi and the drop pill matrix in a ratio of 1:3~3:1 by weight.

32. The QMDP according to the 31$^{st}$ paragraph, wherein the QMDP is prepared by the API of Qishenyiqi and the drop pill matrix in a ratio of 1:(1~3) by weight.

33. The QMDP according to any one of the 30$^{th}$~32$^{nd}$ paragraphs, wherein the particle size of the micro drop pill is 0.2 mm~2 mm.

34. The QMDP according to the 33$^{rd}$ paragraph, wherein the particle size of the micro drop pill is 1 mm~2 mm.

35. The QMDP according to any one of the 30$^{th}$~34$^{th}$ paragraphs, wherein the API of Qishenyiqi is prepared by the following crude drugs by weight parts: Astragalus membranaceus 150~180 parts, Salvia militiorrhiza 75~85 parts, Panax notoginseng 13~18 parts and volatile oil from Lignum dalbergiae odoriferae 0.5~1 parts.

36. The QMDP according to any one of the 30$^{th}$~35$^{th}$ paragraphs, wherein the API of Qishenyiqi is prepared by the following crude drugs by weight parts: Astragalus membranaceus 150 parts, Salvia militiorrhiza 75 parts, Panax notoginseng 15 parts and volatile oil from Lignum dalbergiae odoriferae 1 part.

DETAILED DESCRIPTION OF THE INVENTION

In an embodiment of this invention, the preparation method for preparing the micro drop pill comprises the following steps:

(1) Material melting step: heat melting the medicine and the drop pill matrix at 40° C.~120° C., homogenizing for 0.5~4 hours to obtain a homogenized molten medicine liquid, the ratio of the medicine to the drop pill matrix is 1:5~5:1 by weight;

(2) Dropping step: delivering the molten medicine liquid under pressure to a dripper, and acquiring medicine drops at a vibration frequency for dropping of 2~2000 Hz under a dropping pressure of 0.5~4.0 Bar, the temperature of the dripper of 40° C.~200° C. and the viscosity of the molten medicine liquid of 300~1500 cp; and, (3) Condensation step: cooling the medicine drops with a cooling gas for forming by solidifying, obtaining the micro drop pills having a particle size of 0.2 mm~4 mm, the temperature of the cooling gas is 0° C. or lower.

Wherein, in Step (1), the drop pill matrix includes one or more selected from the group consisting of PEGs, sorbitol, xylitol, lactitol, maltose, starch, methylcellulose, sodium carboxymethyl cellulose, hydroxypropyl methylcellulose (HPMC), arabic gum, alginic acid, dextrin, cyclodextrin, agar and lactose, preferably solid PEGs, such as PEG-1000, PEG-2000, PEG-3000, PEG-4000, PEG-5000, PEG-6000, PEG-7000 and PEG-8000, more preferably one or more selected from the group consisting of PEG-1000, PEG-2000, PEG-3000, PEG-4000, PEG-6000, PEG-8000, most preferably PEG-6000, PEG-4000 or the combination of PEG-4000 and PEG-6000.

In Step (1), the temperature for heat melting preferably is at 60~100° C., more preferably at 65~90° C., further preferably 75~85° C.

In Step (1), the homogenizing time preferably is 1~3 hours, further preferably 2 hours.

In Step (1), the ratio of the medicine to the drop pill matrix is 1:3~3:1 by weight, preferably 1:(1~3) by weight.

In Step (2), the temperature of the dripper is preferably at 60~120° C., preferably at 60~100° C.; the vibration frequency for dropping is preferably at 20~300 Hz, more preferably 50~300 Hz, more preferably 20~200 Hz, more preferably 20~150 Hz, most preferably 50~150 Hz. The vibration mode includes magnetic/electronic vibration or pneumatic vibration. Wherein, in the pneumatic vibration mode, the vibration frequency and the vibration amplitude are larger. If the material viscosity is more than 800 cp, the electronic vibration is incapable of effectively cutting material, resulting in the blockage of the dripper; if this happens, the pneumatic vibration mode can be used. In the present invention, the electronic vibration is preferably employed, the viscosity of the molten medicine liquid preferably is 500~1000 cp, more preferably 700~1000 cp.

During the dropping process, a vibration waveform is used as a PAT (Process Analyzing Technology) index to measure the distribution of the particle size and to monitor the state of fluidization of the drop pills in the real-time manner by using a stroboscopic device.

In Step (3), the condensation by a cooling gas means that the drops are cooled by using a low-temperature condensate trap to form by solidifying. The temperature of the cooling gas is at 0° C.~−150° C., preferably −10° C.~−140° C., further preferably −40° C.~−140° C., further preferably −60° C.~−140° C., most preferably −80° C.~−120° C.; the cooling gas is air, nitrogen or inert gas; the particle size of the micro drop pill is 1.0 mm~2.0 mm, preferably 0.5 mm~2 mm.

In one preferred embodiment of this invention, the preparation method for preparing the micro drop pill comprises the following steps:

(1) Material melting step: heat melting the medicine and the drop pill matrix at 60° C.~100° C., homogenizing for 1~3 hours to obtain a homogenized molten medicine liquid, the ratio of the medicine to the drop pill matrix is 1:3~3:1 by weight;

(2) Dropping step: delivering the molten medicine liquid under pressure to a dripper, and acquiring medicine drops at a vibration frequency for dropping of 20~200 Hz under a dropping pressure of 0.5~4.0 Bar, the temperature of the dripper of 60° C.~120° C. and the viscosity of the molten medicine liquid of 700~1000 cp; and, (3) Condensation step: cooling the medicine drops with a cooling gas for forming by solidifying, obtaining the micro drop pills having a particle size of 0.5 mm~2 mm, the temperature of the cooling gas is 0° C.~−150° C.

In another preferred embodiment of this invention, the preparation method for preparing the micro drop pill comprises the following steps:

(1) Material melting step: charging the medicine and the drop pill matrix into a homogenizer, mixing homogenously at 1000~5000 rpm for 1~200 min, then melting homogenously at 3000~10000 rpm for 1~100 min; during the melting process, the temperature is kept at 60~100° C. to obtain the molten medicine liquid; the ratio of the medicine to the drop pill matrix is 1:5~5:1 by weight;

(2) Dropping step: delivering the molten medicine liquid to a dripper, and acquiring medicine drops by means of vibration dropping at a vibration frequency for dropping of 20~300 Hz under a dropping pressure of 0.5~4.0 Bar and the temperature of the dripper of 40° C.−200° C.; the dropping rate is matched with the melting rate in Step (1); and, (3) Condensation step: cooling the medicine drops with a cooling gas rapidly to solidify, and obtaining solid drop pills having a particle size of 0.2 mm~4.0 mm; the temperature of the cooling gas is 0° C.~−150° C.

Wherein, in Step (1), the ratio of the medicine to the drop pill matrix is 1:3~3:1 by weight, mixing homogeneously 3000~5000 rpm for 10~60 min and melting homogeneously at 4000~9000 rpm for 5~30 min, during the melting process, the temperature is kept at 70~90° C.; most preferably, the ratio of the medicine to the drop pill matrix is 1:(1~3) by weight, mixing homogeneously 3000~4000 rpm for 10~30 min and melting homogeneously at 4000~6000 rpm for 6~30 min, during the melting process, the temperature is kept at 75~85° C.

In Step (2), preferably, the temperature of the dripper is at 70~100° C., the vibration frequency for dropping is at 90~200 Hz, the dropping pressure is at 1.0~3.0 Bar; most preferably, the vibration frequency is at 137 Hz, the acceleration speed is at 4G, the dropping pressure is at 1.8 Bar and temperature of the dripper is at 75~85° C.; Preferably, the dropping rate is 10~40 Kg/h, preferably 12~30 Kg/h, further preferably 15~25 Kg/h. Further, the method can additionally comprise a drying step as Step (4): drying the low-temperature drop pills from Step (3) on a fluidized-bed at 40~150° C., preferably at 40~60° C. for 1~4 hours, preferably 1~3 hours, most preferably 2 hours to obtain the uncoated drop pills.

In Step (4), a gradient-rising temperature drying method is used as follows: fluidizing at −20~30° C., drying at 15~35° C. for 10~120 min, drying at 35~55° C. for 10~60 min, drying at 55~100° C. for 0~60 min; preferably, the gradient-rising temperature drying method is performed as follows: fluidizing at 0~20° C., drying at 25° C. for 60 min, drying at 45° C. for 30 min, drying at 55° C. for 0~30 min.

In Step (4), by screening from a large number of drying methods, the inventors found that: in Step (3), the uncoated drop pill is dried by one of the following drying methods: airing under low-humidity, drying by coating pot, drying by vacuum drying oven, drying by hot air circulation drying oven, drying by track type microwave dryer, drying by fluidized drying coater. In terms of yield and productivity, drying by coating pot, drying by track type microwave dryer, drying by fluidized drying coater are preferred. In terms of industrialization, drying by fluidized-bed is preferred, and drying by fluidized drying coater is more preferred. Advantages and disadvantages of various drying methods are shown in Table 1.

Step (1): adding the medicine powder or extract with water, stirring for 10 min or longer at 30~80° C. to obtain a pre-mixed medicine material, ensuring the homogenization of water content. This step can remedy the defects brought about by feeding dried powder material.

In the present invention, the micro drop pills prepared by the method can be either packaged directly, or prepared into capsule after loading into a capsule shell. In the preparation of capsules, the weighing step for capsules one-by-one may be additionally employed. Before packaging, high-speed

TABLE 1

| Nos. | Drying mode | Advantages | Disadvantages |
| --- | --- | --- | --- |
| 1 | Airing under low-humidity | High yield. The yield is usually about 95% without considering the effect of dropping factor. | (1) Stringent requirement for airing environment, demanding clean air-circulated workshops with a relative humidity of less than 30%, a temperature of higher than 20° C. and a good air circulation; (2) Prolonged drying period, at least 48 hours required when a layer thickness of the drop pills is up to about 2 cm; (3) Large-area workshop is occupied; (4) Regularly turning the drop pills is necessary; (5) Exposing for a long time, the drop pill product is prone to being polluted. |
| 2 | Drying by coating pot | (1) High yield. The yield is usually about 95% without considering the effect of dropping factor; (2) Drying and coating can be achieved in one machine. | (1) Demanding the inlet air having a low humidity, generally no more than 5 g/kg; (2) Low drying efficiency, at least 6 h/batch; (3) Custom-made device; (4) Easily resulting in product rejection due to the adhesion of drop pills. |
| 3 | Drying by vacuum drying oven | None | (1) Low drying efficiency, demanding low-temperature vacuum drying for a long time, at least 30 h/batch; (2) Low-productivity device, the productivity of oven per square meter is difficult to exceed 0.2 kg/h; (3) Easily resulting in adhesion and deformation of drop pills, which is not round in appearance. |
| 4 | Drying by hot air circulation drying oven | None | (1) Low drying efficiency, demanding low-temperature drying for a long time, at least 40 h/batch; (2) Low-productivity device, the productivity of oven per square meter is difficult to exceed 0.1 kg/h; (3) Easily resulting in adhesion and deformation of drop pills, which is not round in appearance; (4) Relative humidity in the drying workshop should be less than 30%. |
| 5 | Drying by track type microwave dryer | High yield, reaching 20 Kg/h | (1) Difficult to control the drying process, easily resulting in adhesion and deformation of drop pills, which is not round in appearance, or product rejection due to charring by drying; (2) Relative humidity in the drying workshop is less than 30%; (3) Unable to remove residual microwave in product. |
| 6 | Drying by fluidized drying coater | (1) High yield, reaching 30 kg/h; (2) Dying and coating in one machine; (3) Round drop pill in appearance; (4) High yield, the yield is usually 98% or higher without considering the effect of dropping factor; (5) Easy to control the drying process, real-time displaying the water-content in the drop pills. | Necessary to control inlet air humidity, generally no more than 7.5 g/kg. |

Further, the preparation method for the micro drop pill can additionally comprise a coating step as Step (5): coating the uncoated drop pills obtained from Step (4) in a state of fluidization; the concentration of the coating liquid is at 15~25 wt %, preferably 18~20 wt %; the coating material is selected from shellac, CAP (cellulose acetate phthalate), methyl acrylate, methyl methacrylate or Opadry; the ratio of the coating material to the uncoated drop pills is 1:50~1:25 by weight.

In the present invention, in order to better implement the preparation method for the micro drop pill, preferably, the method can additionally comprise a pre-mixing step before weighing for the loaded capsules one-by-one is employed so as to eliminate possibly unqualified capsules.

In the present invention, the features of the method are as follows: it is the first time to combine the techniques of vibration dropping and gas cooling with the fluidized drying & coating method creatively and apply to the preparations of drop pills and drop pill capsules. Hence, both producing rate and forming quality of the drop pill are increased.

Further the production process is simplified. The advantages of the present invention are presented as follows:

1. Using a Method of Vibration Dropping Plus Gas Cooling Instead of the Traditional Drop Pill Preparation Method (Gravity Dropping/Pressurized Dropping and Coolant Cooling)

Utilization of gas cooling well meets the requirements of high-speed dropping, preparing a micro drop pill (with a particle size of 2.5 mm or smaller) and increasing drug-loading capacity. As a result, the drug-loading capacity of the drop pill has been increased by folds while the amount of the drop pill matrix and the dosage are reduced dramatically. Moreover, the productivity of the drop pills has been enhanced greatly from the traditional rate of 1~2 pills/s to 1000~1250 pills/s, and the range of the particle size is expanded from 2 mm~4 mm to 0.2 mm~4 mm. It is possible to produce the micro drop pills that can better meet the requirements for capsule loading. By adjusting the vibration parameters and fluidized drug loading coating, the drug-loading capacity can be increased from about 25 wt % of the traditional drop pills to 50 wt % and higher, and the amount of the drop pill matrix is also reduced by leaps and bounds.

2. Instead of the traditional coolant of liquid paraffin and silicone oil etc., the low-temperature air, nitrogen or inert gas are used to cool the drop pills, avoiding the follow-up steps of eliminating residual solvent (e.g. subsequent step of removing oil). Hence, the operation process is simplified and totally no residual organic solvent. The preparation cost is also reduced.

3. By adding fluidized drying & coating process, not only can solve the problems during the storage of the drop pills prepared by air drying method such as possible adhesion of the drop pills from each other, precipitation of components and reduced volatile oil components, but also the drying time can be reduced from 4~24 hours to only 2 hours. By using fluidized coating, the molten medicine liquid was injected to make drug-loading coating, and the drug-loading capacity can be further increased. Also, this technique of injection can be used for coating the drop pills so as to realize the purposes of different techniques (e.g. sustained release coating, film coating and sugar coating etc). Because the fluidization is a mild process, it ensures the water content in the drop pill reaches a stable value, and the uniformity in drug-loading and coating in the drop pills are also improved. Unlike the drop pills prepared by the traditional methods, the fluidization can prevent the drop pills from being cleft and white-dotted, and at the same time, the yield is increased.

Comparison of the physico-chemical parameters between the micro drop pills of the present invention and the current drop pills are summarized in Table 2.

TABLE 2

| | Pill weight & volume | Drug-loading capacity | Appearance | Preparation efficiency | Release rate | Roundness & particle size |
|---|---|---|---|---|---|---|
| Micro drop pills of the present invention | Smaller pill weight, about 4 mg, so the filling amount is more accurate when being filled into capsule shell | Drug-loading 30 wt % (calculated based on dried extract) | gas cooling instead of traditional coolant, ensuring condensation forming effect, overcoming the drawbacks of residual coolant | By using super high-speed vibration dropping device and pressurized dropping mode, ensuring a stable delivery of the material, increasing dropping rate, greatly improving the preparation efficiency. | Mixing the medicine with the drop pill matrix by homogenizer, so the API of the medicine fully dispersed, thus helping drug absorption. Additionally, reduced pill weight makes the filling amount more accurate when being filled into capsule, drug release rate is also accelerated, and thus a clinical efficacy is improved. | Excellent roundness, the drop pill with a particle size of 0.2 mm~4 mm can be prepared. |
| Commercially available drop pills | Larger pill weight, 25 mg~27 mg | Drug-loading 18~20 wt % (calculated based on dried extract) | Residual coolant on the surface of the drop pills | Slower dropping rate than that of the vibration dropping, and complicated process of eliminating the coolants on the surface of the drop pills, time-consuming process. | — | Better roundness, the drop pill with a particle size of 1 mm~2 mm cannot be prepared. |

EXAMPLES

The following examples are offered only for the purposes of detailed explanation of the present invention and are not intended to limit the scope of the invention in any way.

Example 1 Compound *Salvia militiorrhiza* Micro Drop Pill (CSMDP)

Compound *Salvia militiorrhiza* Drop Pill is a TCM developed by Tianjin Tasly Pharmaceutical Co., Ltd, which is proven to have effects of activating blood by removing stasis and stopping pain by regulating Qi, used for treating chest distress and angina pectoris. The main ingredients of Compound *Salvia militiorrhiza* Drop Pill include *Salvia militiorrhiza*, *Panax notoginseng* and borneol. Its pharmacological effects include increasing coronary blood flow, protecting ischemia myocardium by strengthening hypoxia tolerance, preventing thrombosis by anti-platelet aggregation and improving microcirculation etc.

The current Compound *Salvia militiorrhiza* Drop Pill was prepared by the following method: extracting *Salvia militiorrhiza* and *Panax notoginseng* with water to give an extraction liquid, which was followed by concentration to get the extract; mixing the extract with the drop pill matrix, delivering to a dropping machine, into which borneol was added and well mixed to get a material; melting and dropping the material, and cooling the medicine drops by using liquid paraffin as a coolant to obtain Compound *Salvia militiorrhiza* Drop Pill. Although the preparation of Compound *Salvia militiorrhiza* Drop Pill was known as a very mature technique by the person skilled in the art, there were still a lot of problems faced during the preparation process, e.g. large amount of the matrix and a small unit drug-loading capacity.

In the present invention, the CSMDP is prepared by the API of Compound *Salvia militiorrhiza* and the drop pill matrix in a ratio of 1:5~5:1 by weight; preferably 1:3~3:1 by weight; most preferably 1:(1~3) by weight.

The API of Compound *Salvia militiorrhiza* is prepared by the following crude drugs by weight parts:

*Salvia militiorrhiza* 75.0~90.0 parts
*Panax notoginseng* 10.0~25.0 parts
borneol 0.1~4.0 parts.

Preferably, the API of Compound *Salvia militiorrhiza* is prepared by the following crude drugs by weight parts:

*Salvia militiorrhiza* 80.0~86.0 parts
*Panax notoginseng* 15.0~18.0 parts borneol 0.2~2.0 parts.

Most preferably, the API of Compound *Salvia militiorrhiza* is prepared by the following crude drugs by weight parts:

*Salvia militiorrhiza* 82.0~84.0 parts
*Panax notoginseng* 16.0~17.0 parts
borneol 0.4~1.2 parts.

In the present invention, the API of Compound *Salvia militiorrhiza* is believed to be the active pharmaceutical ingredient of CSDP, which is prepared by extracting *Salvia militiorrhiza* and *Panax notoginseng* to give the extract and mixing borneol to obtain the product. The preparation of the API belongs to the prior art, and the API can be prepared by the conventional methods with the crude drugs in the ratios of the present invention, or by the commercially available *Salvia militiorrhiza* extract, *Panax notoginseng* extract and borneol. In order to better achieve the invention, the API of Compound *Salvia militiorrhiza* is preferably prepared by the following method:

(1) Decocting *Salvia militiorrhiza* and *Panax notoginseng* with water under an alkaline condition to give a decoction, filtering the decoction, concentrating and precipitating the filtrate with ethanol to get a supernatant, filtering the supernatant, recovering ethanol and drying to give *Salvia militiorrhiza* and *Panax notoginseng* extract;

(2) Adding the extract of the above step with borneol and mixing to give the API.

Preferably, in Step (1), under an alkaline condition, *Salvia militiorrhiza* and *Panax notoginseng* are decocted for 1~3 times, 1~3 hours each time and the decoction is filtered to get a filtrate (Filtrate I) for later use; dregs of the decoction is further decocted with water for 1~3 times, 1~3 hours each time, the decoction is filtered to get a filtrate (Filtrate II) for later use; Filtrate I and Filtrate II are combined and concentrated to give a concentrated liquid, which is precipitated with ethanol and allows to stand still to get a supernatant; the supernatant is filtered, ethanol therein is recovered, and further concentrated to give the *Salvia militiorrhiza* and *Panax notoginseng* extract.

The alkaline condition includes, but not limited to, one or more kinds alkali selected from the group consisting of sodium bicarbonate, sodium carbonate, disodium hydrogen phosphate, sodium dihydrogen phosphate, sodium hydroxide, potassium hydroxide and magnesium hydroxide; a pH value of 7.5~9.0 is preferred, ensuring sodium danshensu (sodium DL-beta-(3,4-dihydroxyphenyelactate) can be extracted totally.

Preferably, 50~100% (v/v) (most preferably 95% (v/v)) ethanol solution is added to perform ethanol-precipitation, the final content of ethanol preferably is 60~75% (v/v).

The preparation method for preparing the CSMDP comprises the following steps:

(1) Material melting step: charging the API of Compound *Salvia militiorrhiza* and the drop pill matrix in a ratio of 1:5~5:1 by weight into a homogenizer, mixing homogenously at 1000~5000 rpm for 1~200 min, then melting homogenously at 3000~10000 rpm for 1~100 min; during the melting process, the temperature is kept at 60~100° C. to obtain a molten medicine liquid;

(2) Dropping step: delivering the molten medicine liquid to a dripper, and acquiring medicine drops by means of vibration dropping at a vibration frequency of 50~300 Hz under a dropping pressure of 0.5~4.0 Bar, the temperature of the dripper is at 70° C.~200° C.; the dropping rate is matched with the melting rate in Step (1); and, (3) Condensation step: cooling the medicine drops with a cooling gas rapidly to solidify, and obtaining uncoated drop pills having a particle size of 0.2 mm~4 mm; the temperature of the cooling gas is 0° C.~−150° C.

After Step (2) and Step (3), the pill weight is decreased from 23.5~27.5 mg of the traditional drop pill to 3~4 mg, which can be loaded into capsules; in addition, the problem of residual coolant such as liquid paraffin in the current drop pill product can be solved by using gas cooling.

In order to better prove the merits of the micro drop pill in the present invention, the trial was presented as follows:

Trial Example 1 Comparative Study on Effects of Two Kinds of CSDPs on Acute Myocardial Infarction in Rats 1. Animals SD male rats, weighing 340~360 g, were purchased from Beijing Weitonglihua Experimental Animal Co., Ltd, and certification No.: SCXK (Jing) 2007-0001.

2. Drugs, Reagents and Apparatus

CSMDP of the present invention was prepared by the method of Preparative Example 1 of CSMDP.

CSDP, used as a comparative drug, was commercially available in China, prepared by Tianjin Tasly Pharmaceutical Co., Ltd.

Chloral hydrate and triphenyl tetrazolium chloride (TTC) were used for anesthesia.

Apparatus: MedLab-U/8c bio-signals collecting-processing system, purchased from Nanjin Meiyi Inc.

3. Experimental Methods

Grouping: the rats were randomly divided into groups according to their body weight: S group (Sham operation group), M group (Model group), Y group (Positive control group, metoprolol tartrate, Lot No. 1201039), F group (CSMDP of the present invention) and G group (CSDP available in China, Lot No. 2011L16); 10 rats in each group.

Modeling and Administrating Method:

After grouping, the animals were administrated intragastrically for 7 days, which was shown in Table 3. On the 8$^{th}$ day, the rats were anesthetized intraperitoneally with 10% chloral hydrate (3 ml/kg) and fixed on a small wood plate in a supine position. Pins were inserted under the skin of the right forelimb and both hind limbs, and then the rats were connected with the MedLab-U/8c bio-signals collecting-processing system to record ECG of the rats. Hair on the front wall of the left chest was clipped. Oral tracheal cannula was performed and the animal respirator was connected at a respiratory frequency of 80 breaths/min, tidal volume 3 ml/100 g and I:E=1:1. Chest on the left front chest lateral side was incised to cut the 3' rib and the pericardium was carefully lifted with forceps to tear apart. The left main trunk of coronary vein pass between the lower edge of the left atrial appendage and pulmonary artery cone was observed in most of the rats, accompanied with left anterior decending branch (LAD). Medical suture (4-0) was used to transfix LAD and a small amount of myocardial tissue at a distance of about 1~2 mm from the lower edge of the left atrial appendage and inside interventricular sulcus in the vicinity of the left main trunk of coronary vein. The rats with an elevated J point by 0.1 mV in ECG and pale LVAW (left ventricular anterior wall) indicated a successful modeling. Chest was closed layer by layer. The tracheal tube was removed until the voluntary respiration was recovered in the rats. ECG was recorded continuously for 4 hours. Rats were anesthetized, their heart were cut out, sliced and dyed to calculate myocardial infarction rate (MIR). The serum was collected for later use.

MIR (%)=wet weight of the infarction region/wet weight of the whole heart×100%

TABLE 3

Grouping and administration

| Groups | Dosage (mg/kg) | Dose | Pre-administration time |
|---|---|---|---|
| S group(Sham operation group) | 110 | 1 ml/100 g | 7 d |
| M group(Model group) | 223 | 1 ml/100 g | 7 d |
| Y group(Positive control group, metoprolol tartrate) | 4.5 | 1 ml/100 g | 7 d |
| G group(CSDP available in China) | 115 | 1 ml/100 g | 7 d |
| F group(CSMDP of the present invention) | 84 | 1 ml/100 g | 7 d |

TABLE 4

Effect of CSDP in each group on MIR

| Groups | N | Average wet weight of the whole heart (g) | Average wet weight of the infarction region (g) | MIR (%) |
|---|---|---|---|---|
| S group | 8 | 0.8254 ± 0.0294 | 0.0000 ± 0.0000 | 0.00 ± 0.00 |
| M group | 10 | 0.8207 ± 0.0447 | 0.0414 ± 0.0051 | 5.07 ± 0.75 |
| Y group | 9 | 0.8783 ± 0.0571 | 0.0233 ± 0.0038 | 2.65 ± 0.33* |
| G group | 10 | 0.8493 ± 0.0641 | 0.0288 ± 0.0052 | 3.38 ± 0.49*# |
| F group | 10 | 0.8061 ± 0.0668 | 0.0268 ± 0.0054 | 3.32 ± 0.59*# |

Noted:
compared with M group (Model group), $*p < 0.01$;
compared with Y group (Positive control group), $\#p < 0.01$.

4.2 Effect on the Heart Rate in Rats with Myocardial Infarction

As shown in Table 5, the descending order of the heart rate was F group, G group, M group, Y group and S group within the observation period and 0~1 hour after ligation. 1 hour later, the heart rate in each group was decreased. Within the observation period, the variation of heart rate in Y group and S group was relatively stable. There was no significant difference among these groups in heart rate of the rats.

TABLE 5

Effect of the CSDP sample in each group on the heart rate (beat/min)

| Groups | N | 0 s | 5 s | 10 s | 5 min | 10 min | 30 min | 1 h | 2 h | 3 h | 4 h |
|---|---|---|---|---|---|---|---|---|---|---|---|
| S group | 8 | 390 ± 50 | 390 ± 52 | 400 ± 51 | 407 ± 43 | 401 ± 57 | 386 ± 69 | 394 ± 58 | 417 ± 44 | 364 ± 42 | 358 ± 36 |
| M group | 10 | 416 ± 83 | 447 ± 72 | 436 ± 67 | 444 ± 43 | 423 ± 39 | 423 ± 32 | 399 ± 31 | 361 ± 45 | 363 ± 46 | 336 ± 59 |
| Y group | 9 | 377 ± 48 | 423 ± 39 | 419 ± 41 | 424 ± 29 | 431 ± 17 | 413 ± 34 | 421 ± 47 | 416 ± 33 | 380 ± 66 | 395 ± 52 |
| G group | 10 | 431 ± 43 | 452 ± 21 | 444 ± 24 | 445 ± 29 | 424 ± 27 | 422 ± 25 | 397 ± 25 | 392 ± 40 | 347 ± 39 | 331 ± 38 |
| F group | 10 | 449 ± 28 | 498 ± 7 | 468 ± 34 | 474 ± 35 | 466 ± 34 | 426 ± 40 | 412 ± 40 | 388 ± 51 | 377 ± 60 | 365 ± 56 |

4. Results 4.1 Effect on MIR

The results were presented in Table 4. As shown in Table 4, 7 days after pre-administration, MIR in M group (Model group) was significantly higher than the one in S group (Sham operation group), suggesting the successful modeling. MIRs in G group and F group were respectively 3.38% and 3.32%, significantly lower than the one in M group (5.07%), having a significant difference (p<0.01). It was indicated that both samples had a certain effect against the acute myocardial infarction. However, there was no significantly statistical difference (p>0.05) between G group and F group.

5. Conclusions

Under the dosage set in the trial, the medicines in each group were proven to have a certain effect against myocardial infarction in the rats with a coronary artery ligature; especially the CSMDP of the present invention at a dosage of 84 mg/kg had a MIR of 3.38±0.49%, having a similar efficacy of MIR (3.32±0.59%) of the CSDP product commercially available in China at a dosage of 115 mg/kg. Obviously, the CSMDP at a dosage of 84 mg/kg reached the same effect with the CSDP product commercially available in China at a dosage of 115 mg/kg. The CSMDP had a better efficacy than the current CSDP, having the merits such as high bioavailability, reduced administration dosage and good compliance to the patients, etc.

CSMDP Preparative Example 1

The following materials were prepared: 75 g of *Salvia militiorrhiza* and *Panax notoginseng* extract, 7.5 g of borneol and 165 g of PEG-6000.

(1) Pre-mixing step: the API of Compound *Salvia militiorrhiza* was added with water to pre-mix, stirred in a heat-insulated tank at 40±10° C. for 60 min or longer to make the water content of the API of Compound *Salvia militiorrhiza* at 13.0 wt % to give a pre-mixed material of the API of Compound *Salvia militiorrhiza* for later use;

(2) Material melting step: the PEG-6000 was firstly added into a melting tank, pre-molten by heating to 90° C., into which the pre-mixed material of the API of Compound *Salvia militiorrhiza* was added and the resultant material was mixed by a low-speed homogenization (3200 rpm); after mixing, the homogenization rate was increased to 5000 rpm to melt the material for 6 min; during melting process, the temperature of the material was kept at 80±5° C. to give a molten medicine liquid;

(3) Dropping step: the aforesaid molten medicine liquid was delivered to a dripper, the vibration frequency of the dripper was adjusted to 137 Hz and the temperature of the dripper was adjusted to 80° C.; the medicine liquid was flowed under pressure (1.8 Bar) into the dripper, from the bottom of which the medicine liquid was dropped down by means of vibration; the dropping rate was matched with the melting rate in Step (1);

(4) Condensation step: the medicine drops were cooled in a cooling duct with a low-temperature inert gas at −115±5° C. to cool the liquid drops to form solid drop pills;

(5) Drying step: the resultant drop pills were dried in a fluidized state; until the drop pills reached a better fluidized state in the bed of the fluidized bed, the temperature was increased to 25° C. to dry for 60 min, further increased to 45° C. to dry for 30 min, continuously increased to 55° C. to dry for 30 min, and decreased 30° C. or lower to discharge the drop pills. The water content of the drop pills was controlled in the range of 3.0~7.0 wt % to give uncoated drop pills as the intermediate product;

(6) Coating step: the amount of coating powder was calculated based on the coating feed capacity and formulation; Opadry, which has 4 wt % of the weight of the uncoated drop pills, was used to prepare a 18 wt % coating solution and stirred for 45 min; the inlet air temperature was initially set to 25° C.; after the qualified uncoated drop pills were loaded into the fluidized bed, the inlet air temperature was increased to 48° C.; until the temperature of the materials was up to 38° C., the coating was started; the temperature of the material was kept at 35~45° C. during the coating and decreased 30° C. or lower after coating; the drop pills were discharged, screened to give coated drop pills as the intermediate product, the coating weigh of the coated drop pills was controlled in a range of 3.3±0.7 wt % and the water content was controlled in a range of 3.0~7.0 wt %;

(7) Loading into capsule and packaging step: the resultant micro drop pills with a particle size of 1.0 mm~2.0 mm were loaded into capsules; 100% of the capsules were on-line checkweighed with a capsule checkweigher, packaged to give the final product.

Wherein, during the dropping process, the formation of the drop pills was measured visually by using a stroboscopic illumination to perform a real-time monitoring and adjustment. In order to improve the uniformity and roundness of the drop pills, the steps of screening and regulating the drop pills could be added.

Wherein, the API of Compound *Salvia militiorrhiza* was prepared by the following method:

(1) 83.0 kg of *Salvia militiorrhiza* and 16.0 kg of *Panax notoginseng* were decocted with water under an alkaline condition to give a decoction; the decoction was filtered, concentrated and precipitated with ethanol to give a supernatant; the supernatant was filtered, recovered ethanol and dried to give the *Salvia militiorrhiza* and *Panax notoginseng* extract; and, (2) 0.8 kg of borneol was added to the aforesaid *Salvia militiorrhiza* and *Panax notoginseng* extract and well mixed to obtain the API.

Wherein, in Step (1), under an alkaline condition (pH 8.0), *Salvia militiorrhiza* and *Panax notoginseng* were decocted for 2 times, 2 hours each time and filtered to give Filtrate I for later use; dregs of the decoction was further decocted with water for 2 times, 2 hours each time, filtered to give Filtrate II for later use; Filtrate I and Filtrate II were combined and concentrated to give a concentrated liquid, which was added with ethanol to make the final content of ethanol as 70% (v/v) and allowed to stand still to give a supernatant; the supernatant was taken, filtered, ethanol therein was recovered, concentrated and dried to give the *Salvia militiorrhiza* and *Panax notoginseng* extract.

Besides, borneol was commercially available.

CSMDP Preparative Example 2

Except that the *Salvia militiorrhiza* and *Panax notoginseng* extract was prepared by the following crude drugs by weight parts: *Salvia militiorrhiza* 75 parts, *Panax notoginseng* 10 parts, borneol 0.1 parts, and the ratio of the API of Compound *Salvia militiorrhiza* to PEG-6000 was 1:5 by weight, the CSMDP was prepared by the same method as CSMDP PREPARATIVE EXAMPLE 1.

CSMDP Preparative Example 3

Except that the *Salvia militiorrhiza* and *Panax notoginseng* extract was prepared by the following crude drugs by weight parts: *Salvia militiorrhiza* 90 parts, *Panax notoginseng* 25 parts, borneol 4 parts, and the ratio of the API of Compound *Salvia militiorrhiza* to PEG-6000 was 5:1 by weight, the CSMDP was prepared by the same method as CSMDP PREPARATIVE EXAMPLE 1.

CSMDP Preparative Example 4

The following materials were prepared: 75 g of *Salvia militiorrhiza* and *Panax Notoginseng* extract, 7.5 g of borneol and 165 g of a mixture of cyclodextrin and agar (1:1). CSMDP was prepared by the following steps:

(1) Material melting step: the mixture of cyclodextrin and agar (1:1) was used as a matrix, charged into a homogenizer with the API of Compound *Salvia militiorrhiza* to homogenize at 1000 rpm for 1 min to give a material; the material was molten homogenously at 3000 rpm for 1 min; during the melting process, the temperature of the material was kept at 60° C. to obtain a molten medicine liquid;

(2) Dropping step: the molten medicine liquid was delivered to a dripper and dropped by means of vibration dropping at the dripper temperature of 70° C. and a vibration frequency of 50 Hz under a dropping pressure of 0.5 Bar; the dropping rate was matched with the melting rate in Step (1); and, (3) Condensation step: the medicine drops were cooled with a cooling gas rapidly to solidify and obtained uncoated drop pills having a particle size of 0.2 mm; the temperature of the cooling gas was 0° C.

The preparation method for *Salvia militiorrhiza* and *Panax notoginseng* extract was the same as CSMDP PREPARATIVE EXAMPLE 1.

CSMDP Preparative Example 5

The following materials were prepared: 75 g of *Salvia militiorrhiza* and *Panax notoginseng* extract, 7.5 g of borneol and 165 g of a mixture of arabic gum and lactose (1:1). CSMDP was prepared by the following steps:

(1) Material melting step: the mixture of arabic gum and lactose (1:1) was used as a matrix, charged into a homogenizer with the API of Compound *Salvia militiorrhiza* to homogenize at 5000 rpm for 200 min to give a material; the material was molten homogenously at 10000 rpm for 100 min; during the melting process, the temperature of the material was kept at 100° C. to obtain a molten medicine liquid;

(2) Dropping step: the molten medicine liquid was delivered to a dripper and dropped by means of vibration dropping at the dripper temperature of 300° C. and a vibration frequency of 300 Hz under a dropping pressure of 4.0 Bar; the dropping rate was matched with the melting rate in Step (1); and, (3) Condensation step: the medicine drops were cooled with a cooling gas rapidly to solidify and obtained uncoated drop pills having a particle size of 4.0 mm; the temperature of the cooling gas was −150° C.

The preparation method for *Salvia militiorrhiza* and *Panax notoginseng* extract was the same as CSMDP PREPARATIVE EXAMPLE 1.

CSMDP Preparative Example 6

The following materials were prepared: 75 g of *Salvia militiorrhiza* and *Panax notoginseng* extract, 7.5 g of borneol and 165 g of lactitol. CSMDP was prepared by the following steps:

(1) Material melting step: the lactitol was used as a matrix, charged into a homogenizer with the API of Compound *Salvia militiorrhiza* to homogenize at 2500 rpm for 100 min to give a material; the material was molten homogenously at 6000 rpm for 50 min; during the melting process, the temperature of the material was kept at 80° C. to obtain the molten medicine liquid;

(2) Dropping step: the molten medicine liquid was delivered to a dripper and dropped by means of vibration dropping at the dripper temperature of 150° C. and a vibration frequency of 150 Hz under a dropping pressure of 2 Bar; the dropping rate was matched with the melting rate in Step (1);

(3) Condensation step: the medicine drops were cooled with a cooling gas rapidly to solidify to obtained uncoated drop pills having a particle size of 2 mm; the temperature of the cooling gas was −100° C.;

(4) Drying step: the resultant drop pills were dried in a fluidized state by using a fluidized drying device at 50° C. for 2 hours to give dried uncoated drop pills; and, (5) Coating step: the resultant dried uncoated drop pills were coated at 40° C. in fluidized bed to obtain coated drop pills; the ratio of the coating material to the uncoated drop pills was 1:25 by weight; the concentration of the coating solution was 10 wt % and the coating material was Opadry.

The preparation method for *Salvia militiorrhiza* and *Panax notoginseng* extract was the same as CSMDP PREPARATIVE EXAMPLE 1.

CSMDP Preparative Example 7

The following materials were prepared: the API powder of Compound *Salvia militiorrhiza* (including 75 g of *Salvia militiorrhiza* and *Panax notoginseng* extract and 7.5 g of borneol) and 165 g of PEG-8000. CSMDP was prepared by the following steps:

The API powder of Compound *Salvia militiorrhiza* was added with water and stirred at 60° C. for 10 min or longer to obtain a pre-mixed API of Compound *Salvia militiorrhiza*.

(1) Material melting step: the PEG-8000 and the pre-mixed API of Compound *Salvia militiorrhiza* were charged into a homogenizer to homogenize at 2500 rpm for 100 min to give a material; the material was molten homogenously at 6000 rpm for 50 min; during the melting process, the temperature of the material was kept at 80° C. to obtain a molten medicine liquid;

(2) Dropping step: the molten medicine liquid was delivered to a dripper and dropped by means of vibration dropping at a dripper temperature of 150° C. and a vibration frequency of 150 Hz under a dropping pressure of 2 Bar; the dropping rate was matched with the melting rate in Step (1);

(3) Condensation step: the medicine drops were cooled with a cooling gas rapidly to solidify and obtained uncoated drop pills having a particle size of 2 mm; the temperature of the cooling gas was −100° C.;

(4) Drying step: the resultant drop pills were dried in a fluidized state at 50° C. for 2 hours to give the dried uncoated drop pill; and, (5) Coating step: the resultant dried uncoated drop pills were coated at 40° C. in fluidized bed to obtain coated drop pills; the ratio of the coating material to the dried uncoated drop pills was 1:25 by weight; the concentration of the coating solution was 10 wt % and the coating material was shellac.

The preparation method for *Salvia militiorrhiza* and *Panax notoginseng* extract was the same as CSMDP PREPARATIVE EXAMPLE 1.

CSMDP Preparative Example 8

The following materials were prepared: the API powder of Compound *Salvia militiorrhiza* (including 90 g of *Salvia militiorrhiza* and *Panax notoginseng* extract and 2 g of borneol) and 270 g of PEG-1000. CSMDP was prepared by the following steps:

The API powder of Compound *Salvia militiorrhiza* was added with water and stirred at 30° C. for 10 min or longer to obtain a pre-mixed API of Compound *Salvia militiorrhiza*.

(1) Material melting step: the PEG-1000 and the pre-mixed API of Compound *Salvia militiorrhiza* were charged into a homogenizer to homogenize at 2500 rpm for 100 min to give a material; the material was molten homogenously at 6000 rpm for 20 min; during the melting process, the temperature of the material was kept at 100° C. to obtain a molten medicine liquid;

(2) Dropping step: the molten medicine liquid was delivered to a dripper and dropped by means of vibration dropping at a dripper temperature of 70° C. and a vibration frequency of 100 Hz under a dropping pressure of 1.0 Bar and an acceleration speed of 1G and a dropping rate of 10 Kg/h; the dropping rate was matched with the melting rate in Step (1);

(3) Condensation step: the medicine drops were cooled with a cooling gas rapidly to solidify and obtained uncoated drop pills having a particle size of 2 mm; the temperature of the cooling gas was −80° C.;

(4) Drying step: the resultant drop pills were dried by a gradient-rising temperature drying method, fluidized at −20°

C., dried at 15° C. for 10 min, further dried at 35° C. for 10 min, and further dried at 55° C. for 30 min to give dried uncoated drop pills; and, (5) Coating step: the resultant dried uncoated drop pills were coated at 40° C. in a fluidized bed to obtain coated drop pills; the ratio of the coating material to the dried uncoated drop pills was 1:25 by weight; the concentration of the coating solution was 10 wt % and the coating material was cellulose acetate phthalate (CAP).

The preparation method for *Salvia militiorrhiza* and *Panax notoginseng* extract was the same as CSMDP PREPARATIVE EXAMPLE 1.

CSMDP Preparative Example 9

The following materials were prepared: the API powder of Compound *Salvia militiorrhiza* (including 100 g of *Salvia militiorrhiza* and *Panax notoginseng* extract and 5 g of borneol) and 35 g of a mixture of PEG-4000:PEG-6000 (1:1). CSMDP was prepared by the following steps:

The API powder of Compound *Salvia militiorrhiza* was added with water and stirred at 80° C. for 10 min or longer to obtain a pre-mixed API of Compound *Salvia militiorrhiza*.

(1) Material melting step: the mixture of PEG-4000:PEG-6000 (1:1) and the pre-mixed API of Compound *Salvia militiorrhiza* were charged into a homogenizer to homogenize at 2500 rpm for 100 min to give a material; the material was molten homogenously at 6000 rpm for 80 min; during the melting process, the temperature of the material was kept at 80° C. to obtain a molten medicine liquid;

(2) Dropping step: the molten medicine liquid was delivered to a dripper and dropped by means of vibration dropping at a dripper temperature of 100° C. and a vibration frequency of 200 Hz under a dropping pressure of 3.0 Bar and a acceleration speed of 20G and a dropping rate of 40 Kg/h; the dropping rate was matched with the melting rate in Step (1);

(3) Condensation step: the medicine drops were cooled with a cooling gas rapidly to solidify and obtained uncoated drop pills having a particle size of 2 mm; the temperature of the cooling gas was −120° C.;

(4) Drying step: the resultant drop pills were dried by a gradient-rising temperature drying method, fluidized at 30° C., dried at 35° C. for 120 min, at 55° C. for 60 min and at 100° C. for 60 min to give dried uncoated drop pills; and, (5) Coating step: the resultant dried uncoated drop pills were coated at 35° C. in a fluidized bed to obtain coated drop pills; the ratio of the coating material to the dried uncoated drop pills was 1:25 by weight; the concentration of the coating solution was 10 wt % and the coating material was methyl acrylate.

The preparation method for *Salvia militiorrhiza* and *Panax notoginseng* extract was the same as CSMDP PREPARATIVE EXAMPLE 1.

CSMDP Preparative Example 10

The following materials were prepared: 600 g of *Salvia militiorrhiza* and *Panax notoginseng* extract, 5 g of borneol and 600 g of xylitol as the drop pill matrix. CSMDP was prepared by the following steps:

(1) Material melting step: the xylitol was firstly charged into a melting tank and heated to 90° C. to pre-melt, into which the API of Compound *Salvia militiorrhiza* was charged and well mixed to give a molten medicine liquid;

(2) Dropping step: the molten medicine liquid was delivered under pressure to a dripper that was heat-insulated by a steam jacket; at the dripper temperature of 40° C. and a vibration frequency for dropping of 50 Hz, the molten medicine liquid was flowed into the dripper and obtained drops from the bottom of the dripper;

(3) Condensation step: the medicine drops were cooled in a cooling duct with low-temperature inert gas to condensation to obtain solid drop pills; the cooling temperature was −20° C.;

(4) Drying & coating step: the resultant solid drop pills were dried in a fluidized state and drug-loading coated to give coated micro drop pills with a particle size of 0.2 mm~1.0 mm; the drying temperature was 75° C.; and, (5) Packaging step: the coated micro drop pills with a particle size of 0.2 mm~1.0 mm were loaded into capsules; 100% of the capsules were on-line checkweighed with a capsule checkweigher and packaged to give the final product.

The preparation method for *Salvia militiorrhiza* and *Panax notoginseng* extract was the same as CSMDP PREPARATIVE EXAMPLE 1.

Wherein, during the dropping process, the formation of drop pills was measured visually by using a stroboscopic illumination to perform real-time monitoring and adjustment. After the drug-loading coating, in order to improve the uniformity and roundness of the drop pills, the steps of screening and regulating the drop pills could be added.

CSMDP Preparative Example 11

The following materials were prepared: 600 g of *Salvia militiorrhiza* and *Panax notoginseng* extract, 5 g of borneol and 3000 g of a mixture of PEG-6000 and PEG-4000 as the drop pill matrix. CSMDP was prepared by the following steps:

(1) Material melting step: the mixture of PEG-6000 and PEG-4000 was firstly charged into a melting tank and pre-molten by heating to 120° C., into which the API of Compound *Salvia militiorrhiza* was charged and well mixed to give a molten medicine liquid;

(2) Dropping step: the molten medicine liquid was delivered under pressure to a dripper that was heat-insulated by a steam jacket; at a dripper temperature of 80° C. and a vibration frequency for dropping of 20 Hz, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was −80° C.;

(4) Drying & coating step: the resultant solid drop pills were dried in a fluidized state and drug-loading coated to give coated micro drop pills with a particle size of 0.5 mm~1.0 mm; the drying temperature was 150° C.; and, (5) Packaging step: the micro drop pills were loaded into capsules; 100% of the capsules were on-line checkweighed with a capsule checkweigher and packaged to give the final product.

The preparation method for *Salvia militiorrhiza* and *Panax notoginseng* extract was the same as CSMDP PREPARATIVE EXAMPLE 1.

Wherein, during the dropping process, the formation of drop pills was measured visually by using a stroboscopic illumination to perform real-time monitoring and adjustment. After the drug-loading coating, in order to improve the uniformity and roundness of the drop pills, the step of screening and regulating the drop pills could be added.

CSMDP Preparative Example 12

The following materials were prepared: 600 g of *Salvia militiorrhiza* and *Panax notoginseng* extract, 5 g of borneol and 120 g of PEG-1000 as the drop pill matrix. CSMDP was prepared by the following steps:

(1) Material melting step: the PEG-1000 was firstly charged into a melting tank and pre-molten by heating to 40° C., into which the API of Compound *Salvia militiorrhiza* was charged and well mixed to give a molten medicine liquid;

(2) Dropping step: the molten medicine liquid was delivered under pressure to a dripper that was heat-insulated by a steam jacket; at a dripper temperature of 40~60° C. and a vibration frequency for dropping of 200 Hz, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was −100° C.;

(4) Drying & coating step: the resultant solid drop pills were dried in a fluidized state and drug-loading coated, fluidized at 20° C., dried at 25° C. for 60 min, further dried at 45° C. for 30 min and at 55° C. for 30 min to give the coated micro drop pill with a particle size of 3.0 mm~4.0 mm; and, (5) Packaging step: the micro drop pills were loaded into capsules; 100% of the capsules were on-line checkweighed with a capsule checkweigher and packaged to give the final product.

The preparation method for *Salvia militiorrhiza* and *Panax notoginseng* extract was the same as CSMDP PREPARATIVE EXAMPLE 1.

Wherein, during the dropping process, the formation of drop pills was measured visually by using a stroboscopic illumination to perform real-time monitoring and adjustment. In order to improve the uniformity and roundness of the drop pills, the step of screening and regulating the drop pills could be added.

CSMDP Preparative Example 13

The following materials were prepared: 600 g of *Salvia militiorrhiza* and *Panax notoginseng* extract, 5 g of borneol and 3000 g of a mixture of PEG-6000 and PEG-4000 as the drop pill matrix. CSMDP was prepared by the following steps:

(1) Material melting step: the mixture of PEG-6000 and PEG-4000 was firstly charged into a melting tank and pre-molten by heating to 120° C., into which the API of Compound *Salvia militiorrhiza* was charged into a homogenizer to homogenize at 1000 rpm for 1 min and molten homogenously at 3000 rpm for 1 min, during the melting process, the temperature of the material was kept at 60° C. to obtain a molten medicine liquid;

(2) Dropping step: the molten medicine liquid was delivered under pressure to a dripper that was heat-insulated by a steam jacket; at a dripper temperature of 70° C., a vibration frequency for dropping of 50 Hz and a dropping pressure of 0.5 Bar, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was 0° C.;

(4) Drying & coating step: the resultant solid drop pills were dried in a fluidized state and drug-loading coated to give coated micro drop pills with a particle size of 0.2 mm; the drying temperature was 150° C.; and, (5) Packaging step: the micro drop pills were loaded into capsules; 100% of the capsules were on-line checkweighed with a capsule checkweigher and packaged to give the final product.

The preparation method for *Salvia militiorrhiza* and *Panax notoginseng* extract was the same as CSMDP PREPARATIVE EXAMPLE 1.

CSMDP Preparative Example 14

The following materials were prepared: 600 g of *Salvia militiorrhiza* and *Panax notoginseng* extract, 5 g of borneol and 1800 g of PEG-6000 as the drop pill matrix. CSMDP was prepared by the following steps:

(1) Material melting step: the PEG-6000 was firstly charged into a melting tank and pre-molten by heating to 120° C., into which the API of Compound *Salvia militiorrhiza* was charged into a homogenizer to homogenize at 5000 rpm for 200 min and molten homogenously at 10000 rpm for 1 min, during the melting process, the temperature of the material was kept at 100° C. to obtain a molten medicine liquid;

(2) Dropping step: the molten medicine liquid was delivered under pressure to a dripper that was heat-insulated by a steam jacket; at a dripper temperature of 300° C., a vibration frequency of 300 Hz and a dropping pressure of 4.0 Bar, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was −150° C.;

(4) Drying & coating step: the resultant solid drop pills were dried in a fluidized state and drug-loading coated to give coated micro drop pills with a particle size of 4.0 mm; the drying temperature was 150° C.; and, (5) Packaging step: the micro drop pills were loaded into capsules; 100% of the capsules were on-line checkweighed with a capsule checkweigher and packaged to give the final product.

The preparation method for *Salvia militiorrhiza* and *Panax notoginseng* extract was the same as CSMDP PREPARATIVE EXAMPLE 1.

CSMDP Preparative Example 15

The following materials were prepared: 600 g of *Salvia militiorrhiza* and *Panax notoginseng* extract, 5 g of borneol and 2400 g of PEG-4000 as the drop pill matrix. CSMDP was prepared by the following steps:

(1) Material melting step: the PEG-4000 was firstly charged into a melting tank and pre-molten by heating to 120° C., into which the API of Compound *Salvia militiorrhiza* was charged, homogenized at 3000 rpm for 10 min and molten homogenously at 4000 rpm for 5 min, during the melting process, the temperature of the material was kept at 70~90° C. to obtain a molten medicine liquid;

(2) Dropping step: the molten medicine liquid was delivered under pressure to a dripper that was heat-insulated by a steam jacket; at a dripper temperature of 70° C., a vibration frequency for dropping of 90 Hz and a dropping pressure of 1.0 Bar, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was −140° C.; and, (4) Drying step: the resultant solid drop pills were dried in a fluidized state to give uncoated micro drop pills with a particle size of 1.0 mm; the drying temperature was 150° C.

The preparation method for *Salvia militiorrhiza* and *Panax notoginseng* extract was the same as CSMDP PREPARATIVE EXAMPLE 1.

CSMDP Preparative Example 16

The following materials were prepared: 600 g of *Salvia militiorrhiza* and *Panax Notoginseng* extract, 5 g of borneol and 2400 g of PEG-4000 as the drop pill matrix. CSMDP was prepared by the following steps:

(1) Material melting step: the PEG-4000 was firstly charged into a melting tank and pre-molten by heating to 120° C., into which the API of Compound *Salvia militiorrhiza* was charged, homogenized at 4000 rpm for 60 min and molten homogenously at 9000 rpm for 30 min, during the melting process, the temperature of the material was kept at 90° C. to obtain a molten medicine liquid;

(2) Dropping step: the molten medicine liquid was delivered under pressure to a dripper that was heat-insulated by a steam jacket; at a dripper temperature of 100° C., a vibration frequency for dropping of 200 Hz and a dropping pressure of 3.0 Bar, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was −140° C.; and, (4) Drying step: the resultant solid drop pills were dried in a fluidized state to give uncoated micro drop pills with a particle size of 2.0 mm; the drying temperature was 150° C.

The preparation method for *Salvia militiorrhiza* and *Panax notoginseng* extract was the same as CSMDP PREPARATIVE EXAMPLE 1.

CSMDP Preparative Example 17

The following materials were prepared: 600 g of *Salvia militiorrhiza* and *Panax notoginseng* extract, 5 g of borneol and 2000 g of PEG-6000 as the drop pill matrix. CSMDP was prepared by the following steps:

(1) Material melting step: the PEG-6000 was firstly charged into a melting tank and pre-molten by heating to 90° C., into which the API of Compound *Salvia militiorrhiza* was charged and well mixed to give a molten medicine liquid;

(2) Dropping step: the molten medicine liquid was delivered under pressure to a dripper that was heat-insulated by a steam jacket; at dripper temperature of 80° C. and a vibration frequency for dropping of 50 Hz, the molten medicine liquid was flowed into the dripper and obtained medicine drops from the bottom of the dripper;

(3) Condensation step: the medicine drops were cooled with low-temperature inert gas to condensation to obtain solid drop pills; the cooling temperature was −20° C.;

(4) Drying & coating step: the resultant solid drop pills were dried in a fluidized state and drug-loading coated to give coated micro drop pills with a particle size of 1.0 mm~2.0 mm; the drying temperature was 75° C.; and, (5) Packaging step: the coated micro drop pills were loaded into capsules; 100% of the capsules were on-line checkweighed with a capsule checkweigher and packaged to give the final product.

The preparation method for *Salvia militiorrhiza* and *Panax notoginseng* extract was the same as CSMDP PREPARATIVE EXAMPLE 1.

Wherein, during the dropping process, the formation of drop pills was measured visually by using a stroboscopic illumination to perform real-time monitoring and adjustment. In order to improve the uniformity and roundness of the drop pills, the step of screening and regulating the drop pills could be added.

As found by the study of the inventors, compared with the current CSDP, the CSMDP prepared by the methods disclosed in the CSMDP PREPARATIVE EXAMPLES 2~17 had the similar merits such as high bioavailability, reduced administration dosage and good compliance to the patients. Meanwhile, the CSMDP prepared by the methods disclosed in CSMDP PREPARATIVE EXAMPLE 2~17 had the same merits listed in Table 2.

Example 2 QMDP (Qishenyiqi Micro Drop Pill)

Qishenyiqi drop pill is a TCM preparation prepared by *Astragalus membranaceus, Salvia militiorrhiza, Panax notoginseng* and volatile oil from *Lignum dalbergiae odoriferae*. It is capable of significantly improving symptoms such as myocardial injury and heart dysfunction, which has been used clinically for treating diseases of chronic heart failure, myocarditis and its sequelae, myocardial infarction recovery stage and myocardial fibrosis. The current Qishenyiqi drop pill has the merits such as small dosage, convenient administration, rapid dissolution, direct absorption into blood by mucosa, high bioavailability and high efficacy with no gastrointestinal stimulation and no obvious toxic and side effects.

The preparation method for QMDP known in the prior art mainly comprises the following steps: firstly, the following crude drugs were prepared: *Astragalus membranaceus, Salvia militiorrhiza, Panax notoginseng*, volatile oil from *Lignum dalbergiae odoriferae* and PEG-6000; *Salvia militiorrhiza* and *Panax notoginseng* were decocted with water and precipitated with ethanol; the ethanol was recovered and concentrated to obtain the *Salvia militiorrhiza* and *Panax notoginseng* extract; *Astragalus membranaceus* was decocted with water and precipitated with ethanol to obtain deposit of *Astragalus membranaceus*; *Lignum dalbergiae odoriferae* was extracted with water to obtain volatile oil from *Lignum dalbergiae odoriferae*; the *Salvia militiorrhiza* and *Panax notoginseng* extract, the deposit of *Astragalus membranaceus* and PEG-6000 were well molten on a water bath, followed by addition of volatile oil from *Lignum dalbergiae odoriferae* and well mixed and delivered to a dripping machine to prepare drop pills. Although the method was very mature for preparing Qishenyiqi drop pills in the prior art, there were still problems faced during preparation process, e.g. a large amount of the matrix and a small unit drug-loading capacity.

In the present invention, Qishenyiqi micro drop pills are prepared by the API and the drop pill matrix in a ratio of 1:5~5:1 by weight. The API is prepared by the following crude drugs by weight parts:
*Astragalus membranaceus* 100~200 parts;
*Salvia militiorrhiza* 50~100 parts;
*Panax notoginseng* 10~20 parts; and,
Volatile oil from *Lignum dalbergiae odoriferae* 0.5~2 parts.

Preferably, the API is prepared by the following crude drugs by weight parts:
*Astragalus membranaceus* 150~180 parts;
*Salvia militiorrhiza* 75~85 parts;
*Panax notoginseng* 13~18 parts; and,
Volatile oil from *Lignum dalbergiae odoriferae* 0.5~1 parts.

Most preferably, the API is prepared by the following crude drugs by weight parts:
*Astragalus membranaceus* 150 parts;
*Salvia militiorrhiza* 75 parts;
*Panax notoginseng* 15 parts; and,
Volatile oil from *Lignum dalbergiae odoriferae* 1 part.

Preferably, the micro drop pills are prepared by the API and the drop pill matrix in a ratio of 1:3~3:1 by weight, most preferably 1:(1~3) by weight.

In the present invention, the API of Qishenyiqi micro drop pill is used as the active pharmaceutical ingredient, which is prepared by the following steps: *Astragalus membranaceus*, *Salvia militiorrhiza* and *Panax notoginseng* were extracted and followed by addition of volatile oil from *Lignum dalbergiae odoriferae*. The preparation of the API belongs to the prior art, and the API can be prepared by the conventional methods with the crude drugs in the ratios of the present invention, or by the commercially available *Astragalus membranaceus* extract, *Salvia militiorrhiza* extract, *Panax notoginseng* extract and volatile oil from *Lignum dalbergiae odoriferae*. In order to better achieve the present invention, the API is preferably prepared by the following method:

(1) Decocting *Salvia militiorrhiza* and *Panax notoginseng* with water under an alkaline condition to give a decoction, filtering the decoction, concentrating and precipitating the filtrate with ethanol to get a supernatant, filtering the supernatant, recovering ethanol and concentrating to give the *Salvia militiorrhiza* and *Panax notoginseng* extract;

(2) Decocting *Astragalus membranaceus* under an alkaline condition to give a decoction, filtering the decoction, concentrating and precipitating the filtrate with ethanol, filtering the supernatant, recovering ethanol and concentrating to give the *Astragalus membranaceus* extract;

(3) Mixing the *Astragalus membranaceus* extract and *Salvia militiorrhiza* and *Panax notoginseng* extract and then adding the volatile oil from *Lignum dalbergiae odoriferae* to give the API.

Preferably in Step (1), under an alkaline condition, *Salvia militiorrhiza* and *Panax notoginseng* are decocted with water for 1~3 times, 1~3 hours each time to give a decoction, and the decoction was filtered to get a filtrate; the filtrate is concentrated to give a concentrated liquid, into which 70~100% (v/v) ethanol is added to make the final concentration of ethanol 50~70% (v/v) and allow to stand still to get a supernatant; the supernatant is taken, filtered, ethanol is recovered and concentrated to give the *Salvia militiorrhiza* and *Panax notoginseng* extract. Most preferably, *Salvia militiorrhiza* and *Panax notoginseng* are decocted with water and an appropriate amount of alkali for 2 times, 2 hours each time and filtered to get a filtrate for each decoction; the filtrates are combined and concentrated to give a concentrated liquid with a relative density of 1.13~1.23 (80° C.), into which ethanol is added to make a final concentration of ethanol 65~70% (v/v) and allow to stand still for 12 hours or longer to get a supernatant; the supernatant is filtered, ethanol is recovered and concentrated to give the *Salvia militiorrhiza* and *Panax notoginseng* extract with a relative density of 1.30~1.38 (80° C.).

In Step (2), *Astragalus membranaceus* is decocted with an alkaline aqueous solution for 1~3 times, 1~3 hours each time, to give a decoction; the decoction is filtered to give Filtrate I; dregs of the decoction is further decocted with water for 1~3 times, 1~3 hours each time, to give a decoction; the decoction is filtered to give Filtrate II; Filtrate I and Filtrate II are combined and concentrated to give a concentrated liquid, into which 50~100% (v/v) ethanol is added to perform ethanol precipitation for 1~3 times to make the final concentration of ethanol 60~80% (v/v) and allow to stand still to get a supernatant; the supernatant is filtered to give Filtrate III; Filtrate III is recovered and concentrated by ethanol to give the *Astragalus membranaceus* extract.

Most preferably, in Step (2), *Astragalus membranaceus* is decocted with water and an appropriate amount of sodium bicarbonate for 2 hours to give a decoction; the decoction was filtered to give Filtrate I; dregs of the decoction is further decocted with water for 1 hour to give a decoction; the decoction is filtered to give Filtrate II; Filtrate I and Filtrate II are combined and concentrated to give a concentrated liquid with a relative density 1.05~1.20 (75±5° C.), ethanol is added into the concentrated liquid to make the final concentration of ethanol 60±1% (v/v) and allow to stand still for 12 hours or longer to get a supernatant, the supernatant is filtered and recovered ethanol under a reduced pressure to obtain a concentrated liquid with a relative density of 1.18~1.30 (60±5° C.), into which ethanol is added to make the final concentration of ethanol 80±1% (v/v) and allow to stand still for 12 hours or longer to get a supernatant; the supernatant is filtered and concentrated by recovering ethanol under a reduced pressure to give the *Astragalus membranaceus* extract with a relative density of 1.30~1.38 (70±5° C.).

The alkaline condition is at a pH value of 7.5~9.0 and the alkali is, but not limited to, selected from the group consisting of sodium bicarbonate, sodium carbonate, disodium hydrogen phosphate, sodium dihydrogen phosphate, sodium hydroxide, potassium hydroxide and magnesium hydroxide.

The preparation method for preparing the QMDP comprises the following steps:

(1) Material melting step: charging the API and the drop pill matrix in a ratio of 1:5~5:1 by weight into a homogenizer, mixing homogenously at 1000~5000 rpm for 1~200 min, melting homogenously at 3000~10000 rpm for 1~100 min; during the melting process, the temperature of the material is kept at 60~100° C. to obtain a molten medicine liquid;

(2) Dropping step: delivering the molten medicine liquid to a dripper at 70° C.~300° C., and acquiring medicine drops by means of vibration dropping at a vibration frequency of 50~300 Hz under a dropping pressure of 0.5~4.0 Bar; the dropping rate is matched with the melting rate in Step (1);

(3) Condensation step: cooling the medicine drops with a cooling gas rapidly to solidify and obtaining solid uncoated drop pills having a particle size of 0.2 mm~4.0 mm; the temperature of the cooling gas is 0° C.~−150° C.

After Step (2) and Step (3), the pill weight decreased from 23.5~27.5 mg of the traditional drop pills to 3~5 mg, which can be loaded into capsules; the use of gas cooling can solve the problems such as residual coolant of liquid paraffin in the current drop pills.

QMDP Preparative Example 1

The following materials were prepared: 80 g of the API of QMDP and 165 g of PEG-6000.

(1) Pre-mixing step: the API of QMDP was added with water to pre-mix, stirred in a heat-insulated tank at 40±10° C. for 60 min or longer to make the water content of API of QMDP at 13.0 wt % to give a pre-mixed API of QMDP for later use;

(2) Material melting step: the PEG-6000 was firstly added into a melting tank, pre-molten by heating to 90° C., into which the pre-mixed API of QMDP was added, and the resultant material was mixed by a low-speed homogenization (3200 rpm); after mixing, the homogenization rate was increased to 5000 rpm to melt for 6 min; during melting process, the temperature of the material was kept at 80±5° C. to give a molten medicine liquid;

(3) Dropping step: the molten medicine liquid was delivered to a dripper, the vibration frequency of the dripper was adjusted to 137 Hz and the temperature of the dripper was controlled at 80° C.; the molten medicine liquid was flowed into the dripper under pressure (a pressure for dropping is at 0.18 Bar), and obtained medicine drops from the bottom of the dripper;

(4) Condensation step: the medicine drops were cooled in a cooling duct with low-temperature inert gas at −115±5° C. to cool the liquid to form solid drop pills;

(5) Drying step: the resultant drop pills were dried in a fluidized state; until the drop pills reached a better fluidization state in the bed of the fluidized bed, the temperature was increased to 25° C. to dry for 60 min, further increased to 45° C. to dry for 30 min, continuously increased to 55° C. to dry for 30 min, and deceased 30° C. or lower to discharge to give uncoated drop pills as a intermediate product, and the water content of the uncoated drop pills was controlled in a range of 3.0~7.0 wt %;

(6) Coating step: the amount of coating powder was calculated based on the coating feed capacity and formulation; Opadry, which has 4 wt % of the weight of the uncoated drop pills, was used to prepare a 18 wt % coating solution and stirred for 45 min; the inlet air temperature was initially set to 25° C.; after the qualified uncoated drop pills were loaded into the fluidized bed, the inlet air temperature was increased to 48° C.; until the temperature of the drop pills was up to 38° C., the coating was started; the temperature of the material was kept in the range of 35~45° C. during the coating and decreased 30° C. or lower after coating; the drop pills were discharged, screened to give coated drop pills as a intermediate product, the coating weigh of the coated drop pills was controlled in a range of 3.3±0.7% and the water content was controlled in a range of 3.0~7.0 wt %; and, (7) Loading into capsule and packaging step: the resultant micro drop pills with a particle size of 1.0 mm~2.0 mm were loaded into capsules; 100% of the capsules were on-line checkweighed with a capsule checkweigher, packaged to give the final product.

Wherein, during the dropping process, the formation of the drop pills was measured visually by using a stroboscopic illumination to perform a real-time monitoring and adjustment. In order to improve the uniformity and roundness of the drop pills, the steps of screening and regulating the drop pills could be added.

Further, the API of QMDP was prepared by the following method:

(1) 75 weight parts of *Salvia militiorrhiza* and 15 weight parts of *Panax notoginseng* were decocted with water under an alkaline condition to give a decoction; the decoction was filtered, concentrated and precipitated with ethanol to get a supernatant; the supernatant was filtered, recovered ethanol and concentrated to give a *Salvia militiorrhiza* and *Panax notoginseng* extract;

(2) 150 weight parts of *Astragalus membranaceus* was decocted with an alkaline aqueous solution to give a decoction; the decoction was filtered, concentrated and precipitated with ethanol to get a supernatant; the supernatant was filtered, recovered ethanol and concentrated to give a *Astragalus membranaceus* extract;

(3) the *Astragalus membranaceus* extract and the *Salvia militiorrhiza* and *Panax notoginseng* extract were well mixed, and 1 weight part of volatile oil from *Lignum dalbergiae odoriferae* was added to give the API.

Wherein, in Step (1), *Salvia militiorrhiza* and *Panax notoginseng* were decocted with water and an appropriate amount of alkali for 2 times, 2 hours each time to give a decoction, and the decoction was filtered to get filtrates; the filtrates were combined and concentrated to give a concentrated liquid with a relative density of 1.13~1.23 (80° C.); ethanol was added into the concentrated liquid to make a final concentration of ethanol 65~70% (v/v) and allowed to stand still for 12 hours or longer to get a supernatant; the supernatant was filtered, and the ethanol therein was recovered and concentrated to give the *Salvia militiorrhiza* and *Panax notoginseng* extract with a relative density of 1.30~1.38 (80° C.).

Wherein, in Step (2), *Astragalus membranaceus* is decocted with water and an appropriate amount of sodium bicarbonate for 2 hours to give a decoction; the decoction was filtered to give Filtrate I; dregs of the decoction is further decocted with water for 1 hour to give a decoction; the decoction is filtered to give Filtrate II; Filtrate I and Filtrate II are combined and concentrated to give a concentrated liquid with a relative density 1.05~1.20 (75±5° C.), ethanol is added into the concentrated liquid to make the final concentration of ethanol 60±1% (v/v) and allow to stand still for 12 hours or longer to get a supernatant, the supernatant is filtered and recovered ethanol under a reduced pressure to obtain a concentrated liquid with a relative density of 1.18~1.30 (60±5° C.), into which ethanol is added to make the final concentration of ethanol 80±1% (v/v) and allow to stand still for 12 hours or longer to get a supernatant; the supernatant is filtered and concentrated by recovering ethanol under a reduced pressure to give the *Astragalus membranaceus* extract with a relative density of 1.30~1.38 (70±5° C.).

The volatile oil from *Lignum dalbergiae odoriferae* was commercially available.

QMDP Preparative Example 2

The following materials were prepared: 100 g of *Salvia militiorrhiza* and *Panax notoginseng* extract, 200 g of *Astragalus membranaceus* extract, 10 g of volatile oil from *Lignum dalbergiae odoriferae* and 900 g of PEG-6000 as the drop pill matrix.

(1) Material melting step: the PEG-6000 was loaded into a melting tank and pre-molten by heating to 70~80° C., into which a uniform mixture of the *Salvia militiorrhiza* and *Panax notoginseng* extract and the *Astragalus membrana-* ceus extract as well as volatile oil from *Lignum dalbergiae odoriferae* were added, mixed and homogenized to give a molten medicine liquid;

(2) Dropping step: the molten medicine liquid was delivered to a dripper and dropped by means of vibration dropping at a dripper temperature of 80° C. and a vibration frequency of 50 Hz; the dropping rate was matched with the melting rate in Step (1); and, (3) Condensation step: the medicine drops were cooled with a cooling gas rapidly to solidify and obtained solid drop pills; the cooling gas was low-temperature nitrogen at −40° C.;

(4) Drying & coating step: the resultant drop pills was dried in a fluidized state and drug-loading coated at 150° C., screened, regulated and packaged to obtain the final product.

QMDP Preparative Example 3

Except that the API of QMDP was prepared by the following crude drugs by weight parts: *Astragalus membranaceus* 100 parts, *Salvia militiorrhiza* 50 parts, *Panax notoginseng* 10 parts, volatile oil from *Lignum dalbergiae odoriferae* 0.5 parts, and the ratio of the API of QMDP to PEG-6000 was 1:5 by weight, the Qishenyiqi micro drop pills were prepared by the same method as QMDP PREPARATIVE EXAMPLE 1.

QMDP Preparative Example 4

Except that the API of QMDP was prepared by the following crude drugs by weight parts: *Astragalus membranaceus* 200 parts, *Salvia militiorrhiza* 100 parts, *Panax notoginseng* 20 parts, volatile oil from *Lignum dalbergiae odoriferae* 2 parts, and the ratio of the API of QMDP to PEG-6000 was 5:1 by weight, the Qishenyiqi micro drop pills were prepared by the same method as QMDP PREPARATIVE EXAMPLE 1.

QMDP Preparative Example 5

The following materials were prepared: 80 g of the API of QMDP, 165 g of a cyclodextrin and agar (1:1) mixture. The QMDP was prepared by the following method:

(1) Material melting step: the cyclodextrin and agar (1:1) mixture was charged into a homogenizer with the API of QMDP to homogenize at 1000 rpm for 1 min to give a material; the material was molten homogenously at 3000 rpm for 1 min; during the melting process, the temperature of the material was kept at 60° C. to obtain a molten medicine liquid;

(2) Dropping step: the molten medicine liquid was delivered to a dripper and dropped by means of vibration dropping at a dripper temperature of 70° C. and a vibration frequency of 50 Hz under a dropping pressure of 0.5 Bar; the dropping rate was matched with the melting rate in Step (1); and, (3) Condensation step: the medicine drops were cooled with a cooling gas rapidly solidify and obtained uncoated drop pills having a particle size of 0.2 mm; the temperature of the cooling gas was 0° C.

QMDP Preparative Example 6

The following materials were prepared: 80 g of the API of QMDP, 165 g of arabic gum and lactose (1:1) mixture. The QMDP was prepared by the following method:

(1) Material melting step: the arabic gum and lactose (1:1) mixture was charged into a homogenizer with the API of QMDP to homogenize at 5000 rpm for 200 min to give a material; the material was molten homogenously at 10000 rpm for 100 min; during the melting process, the temperature of the material was kept at 100° C. to obtain a molten medicine liquid;

(2) Dropping step: the molten medicine liquid was delivered to a dripper and dropped by means of vibration dropping at a dripper temperature of 300° C. and a vibration frequency of 300 Hz under a dropping pressure of 4.0 Bar; the dropping rate was matched with the melting rate in Step (1); and, (3) Condensation step: the medicine drops were cooled with a cooling gas rapidly to solidify and obtained uncoated drop pills having a particle size of 4.0 mm; the temperature of the cooling gas was −150° C.

QMDP Preparative Example 7

The following materials were prepared: 80 g of the API of QMDP and 165 g of lactitol. The QMDP was prepared by the following method:

(1) Material melting step: the API of QMDP and lactitol were loaded into a homogenizer to homogenize at 2500 rpm for 100 min and molten homogenously at 6000 rpm for 50 min to give a molten medicine liquid; during the melting process, the temperature of the material was kept at 80° C.;

(2) Dropping step: the molten medicine liquid was delivered to a dripper and dropped by means of vibration dropping at a dripper temperature of 150° C. and a vibration frequency of 150 Hz under a dropping pressure of 2 Bar; the dropping rate was matched with the melting rate in Step (1); and, (3) Condensation step: the medicine drops were cooled with a cooling gas rapidly to solidify and obtained the solid uncoated drop pills having a particle size of 2 mm; the temperature of the cooling gas was at −100° C.;

(4) Drying step: the resultant drop pills were dried in a fluidized state by using a fluidized drying device at 50° C. for 2 hours to give dried uncoated drop pills; and, (5) Coating step: the uncoated drop pills were coated at 45° C. on a fluidized bed to give coated drop pills, the ratio of the coating material of shellac to the uncoated drop pills was 1:25 by weight, the coating solution is at 10 wt %.

QMDP Preparative Example 8

The following materials were prepared: 80 g of the API of QMDP powder and 165 g of PEG-8000. The QMDP was prepared by the following method:

The API of QMDP powder was added with water and stirred at 60° C. for 10 min or longer to give a pre-mixed material.

(1) Material melting step: the pre-mixed material and PEG-8000 were loaded into a homogenizer to homogenize at 2500 rpm for 100 min and molten homogenously at 6000 rpm for 50 min to give a molten medicine liquid; during the melting process, the temperature of the material was kept at 80° C.;

(2) Dropping step: the molten medicine liquid was delivered to a dripper and dropped by means of vibration dropping at a dripper temperature of 150° C. and a vibration frequency of 150 Hz under a dropping pressure of 2 Bar; the dropping rate was matched with the melting rate in Step (1); and, (3) Condensation step: the medicine drops were cooled with a cooling gas rapidly to solidify and obtained uncoated drop pills having a particle size of 2 mm; the temperature of the cooling gas was at −100° C.;

(4) Drying step: the resultant drop pills were dried in a fluidized drying device at 50° C. for 2 hours to give dried uncoated drop pills; and, (5) Coating step: the dried uncoated drop pills were coated in a fluidized bed to coat at 35° C. to give coated drop pills; the ratio of the coating material of CAP to the uncoated drop pills was 1:25 by weight; the concentration of coating solution was 25 wt %.

QMDP Preparative Example 9

The following materials were prepared: 90 g of the API of QMDP powder and 270 g of PEG-1000. The QMDP was prepared by the following method:

The API of QMDP powder was added with water and stirred at 30° C. for 10 min or longer to give a pre-mixed material.

(1) Material melting step: the pre-mixed material and PEG-1000 were loaded into a homogenizer to homogenize at 2500 rpm for 100 min and molten homogenously at 6000 rpm for 20 min to give a molten medicine liquid; during the melting process, the temperature of the material was kept at 100° C.;

(2) Dropping step: the molten medicine liquid was delivered to a dripper and dropped by means of vibration dropping at a dripper temperature of 70° C., a vibration frequency of 100 Hz under a dropping pressure of 1.0 Bar, an acceleration speed of 1G and a dropping rate of 10 Kg/h, which was matched with the melting rate in Step (1);

(3) Condensation step: the medicine drops were cooled with a cooling gas rapidly to solidify and obtained uncoated drop pill having a particle size of 2 mm; the temperature of the cooling gas was at −80° C.;

(4) Drying step: the resultant drop pills were dried by a gradient-rising temperature drying method, fluidized at −20° C., dried at 15° C. for 10 min, at 35° C. for 10 min and at 55° C. for 30 min to give dried uncoated drop pills; and, (5) Coating step: the dried uncoated drop pills were coated in a fluidized bed at 40° C. to give coated drop pills; the ratio of the coating material of Opadry to the uncoated drop pill was 1:25 by weight; the concentration of coating solution was 20 wt %.

QMDP Preparative Example 10

The following materials were prepared: 105 g of the API of QMDP powder and 35 g of a PEG-4000 and PEG-6000 (1:1) mixture. The QMDP was prepared by the following method:

The API of QMDP powder was added with water and stirred at 80° C. for 10 min or longer to give a pre-mixed material.

(1) Material melting step: the pre-mixed material and the PEG-4000 and PEG-6000 (1:1) mixture were loaded into a homogenizer to homogenize at 2500 rpm for 100 min and molten homogenously at 6000 rpm for 80 min to give a molten medicine liquid; during the melting process, the temperature of the material was kept at 80° C.;

(2) Dropping step: the molten medicine liquid was delivered to a dripper and dropped by means of vibration dropping at a dripper temperature of 100° C., a vibration frequency of 200 Hz under a dropping pressure of 3.0 Bar, an acceleration speed of 20G and a dropping rate of 40 Kg/h, which was matched with the melting rate in Step (1);

(3) Condensation step: the medicine drops were cooled with a cooling gas rapidly to solidify and obtained uncoated drop pills having a particle size of 2 mm; the temperature of the cooling gas was at −120° C.;

(4) Drying step: the resultant drop pills were dried by a gradient-rising temperature drying method, fluidized at 30° C., dried at 35° C. for 120 min, at 55° C. for 60 min and at 100° C. for 60 min to give dried uncoated drop pills; and, (5) Coating step: the dried uncoated drop pills were coated in a fluidized bed at 35° C. to give coated drop pills; the ratio of the coating material of methyl acrylate to the uncoated drop pills was 1:25 by weight; the concentration of coating solution was 5 wt %.

As found in the study by the inventors, compared with the current Qishenyiqi drop pills, the Qishenyiqi micro drop pills prepared by the methods disclosed in QMDP PREPARATIVE EXAMPLES 1~10 had the same merits listed in Table 2.

Example 3 *Salvia militiorrhiza* Micro Drop Pill (SMDP)

SMDP Preparative Example 1

600 g of the *Salvia militiorrhiza* extract was added with water (60 g) and 1500 g of PEG-6000, charged into a melting tank and totally molten and mixed to give a molten medicine liquid by heating to 90° C. The molten medicine liquid was delivered under pressure to a dripper and dropped by means of vibration dropping at a dripper temperature of 80° C. and a vibration frequency of 20 Hz, the dripper was heated and preserved by infrared ray. The medicine drops were cooled with low-temperature nitrogen and the cooling temperature was −10° C. The drop pills were dried and drug-loading coated in a fluidized bed, screened, regulated and packaged to give the final product.

Wherein, the *Salvia militiorrhiza* extract can either be prepared by the conventional methods or commercially available.

SMDP Preparative Example 2

600 g of the *Salvia militiorrhiza* extract was added with water (60 g) and 600 g of PEG-6000, charged into a melting tank and totally molten and mixed to give a molten medicine liquid by heating to 90° C.~100° C. The molten medicine liquid was delivered under pressure to a dripper and dropped by means of vibration dropping at a dripper temperature of 80° C.~100° C. and a vibration frequency of 150 Hz. The drops were cooled with low-temperature nitrogen and the cooling temperature was −140° C. The drop pills were dried with a fluidized bed at 150° C. and coated with a coating solution (18~20 wt %), screened, regulated and packaged to give the final product.

Wherein, the *Salvia militiorrhiza* extract can either be prepared by the conventional methods or commercially available.

Example 4 Huoxiangzhengqi Micro Drop Pill (HMDP)

HMDP Preparative Example 1

200 g of Huoxiangzhengqi extract, 1 ml of patchouli oil, 2 ml of *perilla* leaf oil and 600 g of PEG-6000 were charged into a melting tank and molten by heating to 65° C.–85° C. to give an uniform liquid. The vibration frequency of an electronic dripper was adjusted to 200 Hz. The temperature of the dripper was controlled at 80° C. The molten medicine liquid was flowed under pressure into the dripper and dropped from the bottom of the dripper into a cooling duct. The drops were cooled with low-temperature nitrogen to give solid drop pills. The cooling temperature was −20° C. The drop pills were dried in a fluidized state at 60° C. and coated with a coating solution (15 wt %). The drop pills were screened, regulated and packaged to obtain the final product.

Wherein, the Huoxiangzhengqi extract can be prepared by the methods disclosed in Chinese patent applications CN 100563635A and CN 1745799A and patchouli oil and *perilla* leaf oil were commercially available.

HMDP Preparative Example 2

200 g of Huoxiangzhengqi extract, 1 ml of patchouli oil, 2 ml of *perilla* leaf oil and 600 g of PEG-6000 were prepared. All of the Huoxiangzhengqi extract and 550 g of PEG-6000 was charged into 1# melting tank and molten by heating to 65~85° C. to give a uniform liquid. 1 ml of patchouli oil, 2 ml of *perilla* leaf oil and 50 g of PEG-6000 were charged into 2# melting tank and molten by heating to 65~85° C. to give a uniform liquid. The liquid in 2# melting tank was delivered to the inner layer of a double-layer dripper and the liquid in 1# melting tank was delivered to the outer layer of the double-layer dripper. The vibration frequency of the dripper was adjusted to 200 Hz. The molten medicine liquid was flowed under pressure into the dripper and dropped by means of vibration dropping at a dripper temperature of 80° C. The drops were cooled with low-temperature air to give solid drop pills. The cooling temperature was −40° C. By using the same method as HMDP PREPARATIVE EXAMPLE 1, the drop pills were dried in a fluidized state and drug-loading coated, screened, regulated and packaged to obtain the final product.

Wherein, the Huoxiangzhengqi extract can be prepared by the methods disclosed in Chinese patent applications CN 100563635A and CN 1745799A and the patchouli oil and *perilla* leaf oil were commercially available.

Example 5 Andrographolide Micro Drop Pill (AMDP)

AMDP Preparative Example 1

400 g of andrographolide, 800 g of PEG-6000 and 800 g of PEG-4000 were prepared. The PEG-6000 and PEG-4000 were charged into a melting tank and pre-molten by heating to 70~80° C., into which the andrographolide was added and mixed to give a uniform liquid. The vibration frequency of a pneumatic dripper was adjusted to 30 Hz. The temperature of the dripper was controlled at 80° C. The molten medicine liquid was flowed under pressure into the dripper and dropped from the bottom of the dripper into a cooling duct. The drops were cooled with low-temperature nitrogen to give solid drop pills. The cooling temperature was −20° C. The drop pills were dried in a fluidized state and coated with a coating solution (25 wt %). The drop pills were screened, regulated and packaged to obtain the final product.

AMDP Preparative Example 2

400 g of andrographolide and 400 g of starch were prepared. The starch was charged into a melting tank and pre-molten by heating to 70~80° C., into which the andrographolide was added and mixed to give a uniform liquid. The vibration frequency of a pneumatic dripper was adjusted to 30 Hz. The temperature of the dripper was controlled at 80° C. The molten medicine liquid was flowed under pressure into the dripper and dropped from the bottom of the dripper into a cooling duct. The drops were cooled with low-temperature nitrogen to give solid drop pills. The cooling temperature was −20° C. The drop pills were dried in a fluidized state and drug loading coated. The drop pills were screened, regulated and packaged to obtain the final product with a particle size of drop pill of 0.5 mm~1 mm.

AMDP Preparative Example 3

1200 g of andrographolide and 400 g of carboxymethyl cellulose (CMC) were prepared. The CMC was charged into a melting tank and pre-molten by heating to 90~100° C., into which the andrographolide was added and mixed to give a uniform liquid. The vibration frequency of a pneumatic dripper was adjusted to 30 Hz. The temperature of the dripper was controlled at 80° C. The molten medicine liquid was flowed under pressure into the dripper and dropped from the bottom of the dripper into a cooling duct. The drops were cooled with low-temperature nitrogen to give solid drop pills. The cooling temperature was −20° C. The drop pills were dried in a fluidized state and drug loading coated. The drop pills were screened, regulated and packaged to obtain the final product with a particle size of drop pill of 1.5 mm~2 mm.

The andrographolide was either prepared by the methods known in the prior art or commercially available.

Example 6 Compound *Ginkgo biloba* Micro Drop Pill (CGMDP)

CGMDP Preparative Example 1

600 g of *Salvia militiorrhiza* and *Ginkgo biloba* extract and 2000 g of PEG-6000 were prepared. The PEG-6000 was charged into a melting tank and pre-molten by heating to 90° C., into which the *Salvia militiorrhiza* and gingko extract was added and mixed to give a uniform liquid. The vibration frequency of a pneumatic dripper was adjusted to 50 Hz. The temperature of the dripper was controlled at 80° C. The molten medicine liquid was flowed under pressure into the dripper and dropped from the bottom of the dripper into a cooling duct. The drops were cooled with low-temperature inert gas to give solid drop pills. The cooling temperature was −20° C. The drop pills were dried in a fluidized state at 75° C. and drug loading coated to obtain drop pills with a particle size of 1.0 mm~2.0 mm. The drop pills were loaded into capsules, and 100% of the capsules were on-line check-weighed with a capsule checkweigher, packaged to give the final product.

Wherein, the *Salvia militiorrhiza* and *Ginkgo biloba* extract was prepared by the method of Chinese patent CN 1872099B.

During the process of dropping, the formation of drop pills was measured visually by using a stroboscopic illumination to perform real-time monitoring and adjustment. In order to improve the uniformity and roundness of the drop pills, the step of screening and regulating could be added.

CGMDP Preparative Example 2

600 g of *Salvia militiorrhiza* and *Ginkgo biloba* extract and 2000 g of PEG-6000 were prepared. The PEG-6000 was charged into a melting tank and pre-molten by heating to 90° C., into which the *Salvia militiorrhiza* and *Ginkgo biloba* extract was added and mixed to give a uniform liquid. The vibration frequency of a pneumatic dripper was adjusted to 50 Hz. The temperature of the dripper was controlled at 80° C. The molten medicine liquid was flowed under pressure into the dripper and dropped from the bottom of the dripper into a cooling duct. The drops were cooled with low-temperature inert gas to give solid drop pills. The cooling temperature was −20° C. The drop pills were dried in a fluidized state at 75° C. and drug loading coated to obtain drop pills with a particle size of 1.0 mm~2.0 mm. The drop pills were loaded into capsules, and 100% of the capsules were on-line checkweighed with a capsule checkweigher, packaged to give the final product.

Wherein, the *Salvia militiorrhiza* and *Ginkgo biloba* extract was prepared by the method of Chinese patent CN 101015527B.

During the process of dropping, the formation of drop pills was measured visually by using a stroboscopic illumination to perform real-time monitoring and adjustment. In order to improve the uniformity and roundness of the drop pills, the step of screening and regulating could be added.

Example 7 Guanxindanshen Micro Drop Pill (GMDP)

600 g of *Salvia militiorrhiza* and *Panax notoginseng* extract, 5 g of volatile oil from *Lignum dalbergiae odoriferae* and 2000 g of PEG-6000 were prepared. The PEG-6000 was charged into a melting tank and pre-molten by heating to 90° C., into which the *Salvia militiorrhiza* and *Panax notoginseng* extract and the volatile oil from *Lignum dalbergiae odoriferae* were added and mixed to give a uniform liquid. The vibration frequency of a pneumatic dripper was adjusted to 50 Hz. The temperature of the dripper was controlled at 80° C. The molten medicine liquid was flowed under pressure into the dripper and dropped from the bottom of the dripper into a cooling duct. The drops were cooled with low-temperature inert gas to give solid drop pills. The cooling temperature was −20° C. The drop pills were dried in a fluidized state at 75° C. and drug loading coated to obtain drop pills with a particle size of 1.0 mm~2.0 mm. The drop pills were loaded into capsules, and 100% of the capsules were on-line checkweighed with a capsule checkweigher, packaged to give the final product.

Wherein, the *Salvia militiorrhiza* and *Panax notoginseng* extract and volatile oil from *Lignum dalbergiae odoriferae* were commercially available. Also, the *Salvia militiorrhiza* and *Panax notoginseng* extract can be prepared by the method for preparing the *Salvia militiorrhiza* and *Panax notoginseng* extract in the preparation of the CSMDP or QMDP.

During the process of dropping, the formation of drop pills was measured visually by using a stroboscopic illumination to perform real-time monitoring and adjustment. In order to improve the uniformity and roundness of the drop pills, the step of screening and regulating could be added.

Example 8 Xuesaitong Micro Drop Pill (XMDP)

400 g of *Panax notoginseng* saponins (PNS) and 400 g of starch were prepared. The starch was charged into a melting tank and pre-molten by heating to 70~80° C., into which the PNS was added and mixed to give a uniform liquid. The vibration frequency of a pneumatic dripper was adjusted to 30 Hz. The temperature of the dripper was controlled at 80° C. The molten medicine liquid was flowed under pressure into the dripper that was heat-insulated by a steam jacket and dropped from the bottom of the dripper into a cooling duct. The drops were cooled with low-temperature nitrogen to give solid drop pills. The cooling temperature was −20° C. The drop pills were dried in a fluidized state, drug loading coated and packaged to obtain drop pills with a particle size of 0.5 mm~1 mm.

As found in the study by the inventors, compared with the current drop pill, the micro drop pills prepared by the methods disclosed in EXAMPLES 3~8 had the same merits listed in Table 2.

What is claimed is:

1. A preparation method for a Chinese medicine micro drop pill comprising the following steps:
    (1) a material melting step comprising heat melting a medicine and a drop pill matrix at 40° C.–120° C. and homogenizing to obtain a homogenized molten medicine liquid, and the ratio of the medicine to the drop pill matrix is 1:3-5:1 by weight;
    (2) a dropping step comprising delivering the molten medicine liquid under pressure to a dripper, and acquiring medicine drops of the molten medicine liquid by vibration dropping at a vibration frequency for dropping of 20-300 Hz under a dropping pressure of 0.5-4.0 Bar, a temperature of the dripper of 40° C.–200° C. and a viscosity of the molten medicine liquid of 300-1500 cp;
    (3) a condensation step comprising cooling the medicine drops with a cooling gas to obtain micro drop pills having a particle size of 0.2 mm-2.5 mm, wherein the temperature of the cooling gas is −40° C. to −200° C. to produce low temperature micro drop pills; and
    (4) a drying step comprising drying the low-temperature micro drop pills from Step (3) on a fluidized-bed to obtain uncoated micro drop pills with a water content of 3%-7%, using a gradient-rising temperature drying method comprising first fluidizing at −20-30° C., then sequentially drying at 15-35° C. for 10-120 minutes (min), 35-55° C. for 10-60 min, and 55-100° C. for 0-60 min.

2. The preparation method according to claim 1, wherein in Step (1), the drop pill matrix comprises PEGs, sorbitol, xylitol, lactitol, maltose, starch, methylcellulose, sodium carboxymethyl cellulose, hydroxypropyl methylcellulose, arabic gum, alginic acid, dextrin, cyclodextrin, agar, lactose or any combination thereof.

3. The preparation method according to claim 1, wherein in Step (2), the dripper is at a temperature of 60-120° C.; the vibration frequency for dropping is 50-300 Hz; and the vibration dropping comprises magnetic/electronic vibration or pneumatic vibration; and, the molten medicine liquid has a viscosity of 500-1000 cp.

4. The preparation method according to claim 1, wherein:
    (1) the material melting step comprises placing the medicine and the drop pill matrix into a homogenizer, mixing homogenously at 1000-5000 rpm for 1-200 min, then melting homogenously at 3000-10000 rpm for 1-100 min, wherein during melting the temperature is kept at 60-100° C. to obtain the molten medicine liquid, and wherein the ratio of the medicine to the micro drop pill matrix is 1:3-5:1 by weight;
    (2) the dropping step comprises delivering the molten medicine liquid under pressure to the dripper, and acquiring medicine drops from the dripper using vibration dropping at a vibration frequency for dropping of 50-300 Hz under a dropping pressure of 0.5-4.0 Bar, wherein the dripper is at a temperature of 40° C.–200° C., and wherein a dropping rate is matched with melting rate of Step (1); and (3) the condensation step comprises cooling the medicine drops with a cooling gas rapidly to solidify, and obtaining solid drop pills having a particle size of 0.2 mm-2.5 mm, wherein the temperature of the cooling gas is –60° C. to –150° C.;

(4) a drying step comprises drying the low-temperature micro drop pills from Step (3) on a fluidized-bed to obtain uncoated micro drop pills with a water content of 3%-7%, wherein a gradient-rising temperature drying method is used, and wherein the gradient-rising temperature drying method comprises first fluidizing at –20-30° C., and then sequentially drying at 15-35° C. for 10-120 min, 35-55° C. for 10-60 min, and 55-100° C. for 0-60 min.

5. The preparation method according to claim 4, wherein in Step (1), the ratio of the medicine to the drop pill matrix is 1:2.3-3:1 by weight, and wherein Step (1) comprises mixing homogeneously at 3000-5000 rpm for 10-60 min, then melting homogeneously at 4000-9000 rpm for 5-30 min, and wherein during the melting process, the temperature is kept at 70° C.–90° C.

6. The preparation method according to claim 4, wherein in Step (1), the ratio of the medicine to the drop pill matrix is 1: (1-3) by weight, and wherein Step (1) comprises mixing homogeneously at 3000-4000 rpm for 10-30 min, then melting homogeneously at 4000-6000 rpm for 6-30 min, and wherein during the melting process, the temperature is kept at 75° C.–85° C.

7. The preparation method according to claim 4, wherein in Step (2), the temperature of the dripper is at 70° C.–100° C., the vibration frequency is at 90-200 Hz, and the dropping pressure is at 1.0-3.0 Bar.

8. The preparation method according to claim 4, wherein in Step (2), the dropping rate is 10-40 Kg/h.

9. The preparation method according to claim 1, wherein the method additionally comprises:

(5) a coating step comprising coating the uncoated drop pills obtained from Step (4) in a state of fluidization, wherein the coating liquid is at a concentration of 15 wt %-25 wt %; and the ratio of coating material to the uncoated drop pill is 1:50-1:25 by weight.

10. The preparation method according to claim 1, wherein in Step (1), the medicine and the drop pill matrix are added with water, and then the medicine, the drop pill matrix and the water are melted with heat.

11. The preparation method according to claim 1, wherein the gradient-rising temperature drying method is: fluidizing at 0-20° C., drying at 25° C. for 60 min, drying at 45° C. for 30 min, and drying at 55° C. for 0-30 min.

12. The preparation method according to claim 4, wherein the gradient-rising temperature drying method is: fluidizing at 0-20° C., drying at 25° C. for 60 min, drying at 45° C. for 30 min, and drying at 55° C. for 0-30 min.

13. The preparation method according to claim 1, wherein, micro drop pill weight obtained at step (3) is 3 mg-5 mg.

14. The preparation method according to claim 9, wherein the coating material comprises a shellac, CAP, methyl acrylate, or methyl methacrylate.

15. The preparation method according to claim 1, wherein the Chinese medicine micro drop pill is a Compound *Salvia militiorrhiza* micro drop pill (CSMDP), a Qishenyiqi micro drop pill (QMDP), a *Salvia militiorrhiza* micro drop pill (SMDP), a Huoxiangzhengqi micro drop pill (HMDP), a *Andrographis paniculata* micro drop pill (AMDP), a Compound *Ginkgo biloba* micro drop pill (CGMDP), a Guanxindanshen micro drop pill (GMDP) or a Xuesaitong micro drop pill (XMDP).

* * * * *